(12) United States Patent
Uri et al.

(10) Patent No.: US 12,201,974 B2
(45) Date of Patent: Jan. 21, 2025

(54) MICROFLUIDIC PROBE HEAD WITH ASPIRATION POSTS

(71) Applicant: Bio-Rad Laboratories, Inc., Hercules, CA (US)

(72) Inventors: Yochanan Uri, Givat Ella (IL); Itay Barak, Haifa (IL); Robert Lovchik, Schönenberg (CH); David P. Taylor, Thalwil (CH); Marcel Buerge, Wisen (CH); Govind V. Kaigala, Pfäffikon (CH)

(73) Assignee: Bio-Rad Laboratories, Inc., Hercules, CA (US)

(*) Notice: Subject to any disclaimer, the term of this patent is extended or adjusted under 35 U.S.C. 154(b) by 187 days.

(21) Appl. No.: 16/984,852

(22) Filed: Aug. 4, 2020

(65) Prior Publication Data
US 2020/0360924 A1    Nov. 19, 2020

Related U.S. Application Data

(63) Continuation of application No. PCT/IB2019/000007, filed on Feb. 5, 2019.
(Continued)

(51) Int. Cl.
    *B01L 3/00*    (2006.01)
(52) U.S. Cl.
    CPC ... *B01L 3/502707* (2013.01); *B01L 3/502769* (2013.01); *B01L 2200/0636* (2013.01); *B01L 2400/049* (2013.01)
(58) Field of Classification Search
    CPC ......... B01L 2200/141; B01L 3/502761; B01L 2200/0647; B01L 2200/027;
    (Continued)

(56) References Cited

U.S. PATENT DOCUMENTS 8,276,760 B2   10/2012  Lean et al.
8,546,084 B2   10/2013  Chaibi
(Continued)

FOREIGN PATENT DOCUMENTS

CN    104321271 A    1/2015
KR    20170143310 A  12/2017
(Continued)

OTHER PUBLICATIONS

C. M. Perrault, M. A. Qasaimeh, T. Brastaviceanu, K. Anderson, Y. Kabakibo et al., "Integrated microfluidic probe station", Nov. 18, 2010, Review of Scientific Instruments, alp, Melville, NY, US, vol. 81, No. 11, pp. 115107-01-115107-08 (Year: 2010).*
(Continued)

*Primary Examiner* — Lyle Alexander
*Assistant Examiner* — Mickey Huang
(74) *Attorney, Agent, or Firm* — Kilpatrick Townsend & Stockton LLP

(57) ABSTRACT

The present disclosure is notably directed to a microfluidic probe head (202), or MFP head, comprising a processing surface (204) having liquid injection and liquid aspiration apertures, as well as projections (205) extending from the processing surface (204). The arrangement of injection and aspiration apertures provides for a hydrodynamic flow confinement within a processing region that is formed between the processing surface (204) and a substrate (104) or sample surface (for example, the bottom of a microtiter plate sample well (102)), typically located beneath the processing surface (204). The disclosure is further directed to related microfluidic probe devices, and methods of operation of such an MFP head, notably to deposit cells on a surface.

21 Claims, 9 Drawing Sheets

Related U.S. Application Data

(60) Provisional application No. 62/626,606, filed on Feb. 5, 2018.

(58) Field of Classification Search
CPC ....... B01L 3/502769; B01L 2200/0636; B01L 2200/0642
See application file for complete search history.

(56) References Cited

U.S. PATENT DOCUMENTS

| | | | |
|---|---|---|---|
| 2010/0176089 A1* | 7/2010 | Delamarche | B01J 19/0046 216/90 |
| 2013/0333761 A1 | 12/2013 | Delamarche et al. | |
| 2015/0075565 A1* | 3/2015 | Foucault | B08B 3/04 134/21 |
| 2015/0140579 A1 | 5/2015 | Chaibi et al. | |
| 2015/0376796 A1 | 12/2015 | Uchiyama et al. | |
| 2016/0168681 A1 | 6/2016 | Duerig et al. | |
| 2017/0304821 A1 | 10/2017 | Kaigala et al. | |
| 2017/0370951 A1 | 12/2017 | Buffiere et al. | |
| 2019/0366341 A1 | 12/2019 | Cho et al. | |
| 2020/0360925 A1 | 11/2020 | Frisan et al. | |
| 2020/0363434 A1 | 11/2020 | Buffiere et al. | |

FOREIGN PATENT DOCUMENTS

| | | |
|---|---|---|
| WO | 2016113691 A1 | 7/2016 |
| WO | 2019149955 A1 | 8/2019 |

OTHER PUBLICATIONS

Yao Chen, Pooya Sareh, Jian Feng, "Effective insights into the geometric stability of symmetric skeletal structures under symmetric variations", Sep. 2015, International Journal of Solids and Structure, vol. 69-70, pp. 277-290 (Year: 2015).*

Arthur Queval "Design and Fabrication of a PDMS Microfluidic Probe and Perfusion Chamber for Microfluidic Experiments With Organotypic Brain Slices", Oct. 16, 2008, Twelfth International Conference on Miniatured Systems of Chemistry and Life, San Diego California, p. 1664-1665 (Year: 2008).*

David Juncker, Heinz Schmid, Emmanuel Delamarche, "Multipurpose microfludic probe", Jul. 24, 2005, Nature Materials, Nature Publishing Group, Longdon, GB, vol. 4 No. 8, pp. 622-627 (Year: 2005).*

Qasaimeh et al., Microfluidic quadrupole and floating concentration gradient, nature communications (Year: 2011).*

Brimmo et al., Microfluidic Probes and Quadrupoles: A new era of open microfluidics, IEEE Xplore (Year: 2017).*

Safavieh et al., "Two-Aperture Microfluidic Probes as Flow Dipoles: Theory and Applications", 2015, Scientific Reports, 5, Article No. 11943 (2015) (Year: 2015).*

International Search Report and Written Opinion mailed Jun. 26, 2019 in International Patent Application No. PCT/EP2019/052743. 14 pages.

International Preliminary Report on Patentability mailed Aug. 20, 2020 in International Patent Application No. PCT/EP2019/052743. 11 pages.

International Search Report and Written Opinion mailed May 16, 2019 in International Patent Application No. PCT/IB2019/000007. 13 pages.

International Preliminary Report on Patentability mailed Aug. 20, 2020 in International Patent Application No. PCT/IB2019/000007. 10 pages.

International Search Report and Written Opinion mailed Mar. 8, 2016 in International Patent Application No. PCT/IB2016/050157. 12 pages.

International Preliminary Report on Patentability mailed Jul. 18, 2017 in International Patent Application No. PCT/IB2016/050157. 10 pages.

Communication pursuant to Article 94(3) EPC dated Jun. 2, 2021 in EP Patent Application No. 19708944.4. 5 pages.

Communication pursuant to Article 94(3) EPC dated Jun. 16, 2021 in EP Patent Application No. 19708889.1. 6 pages.

Autebert, Julien et al.; "Hierarchical Hydrodynamic Flow Confinement: Efficient Use and Retrieval of Chemicals for Microscale Chemistry on Surfaces"; Langmuir; 2014; vol. 30, No. 12; pp. 3640-3645.

Juncker, David et al.; "Multipurpose microfluidic probe"; Nature Materials; Advance Online Publication (8 pages); Published: Jul. 24, 2005; vol. 4, No. 8; pp. 622-628.

Queval, Arthur et al.; "Design and Fabrication of a PDMS Microfluidic Probe and Perfusion Chamber for Microfluidic Experiments With Organotypic Brain Slices"; Twelfth International Conference on Miniaturized Systems for Chemistry and Life Sciences, MicroTAS 2008—San Diego, CA, USA; Duration: Oct. 12-16, 2008; Published: 2008; pp. 1663-1665.

Perrault, Cecile M. et al.; "Integrated microfluidic probe station"; Review of Scientific Instruments; Nov. 2010; vol. 81, No. 11; pp. 115107-1 to 115107-8 (9 pages).

Gervais, Thomas et al.; "Systematic analysis of microfluidic probe design and operation"; 2014 36th Annual International Conference of the IEEE Engineering in Medicine and Biology Society; Published: 2014; pp. 1567-1570 (5 pages).

Restriction Requirement dated Jan. 10, 2019 in U.S. Appl. No. 15/543,579, filed Jul. 14, 2017. 6 pages.

Non-Final Office Action dated Jun. 3, 2019 in U.S. Appl. No. 15/543,579, filed Jul. 14, 2017. 11 pages.

Final Office Action dated Dec. 10, 2019 in U.S. Appl. No. 15/543,579, filed Jul. 14, 2017. 9 pages.

Notice of Allowance dated Jun. 26, 2020 in U.S. Appl. No. 15/543,579, filed Jul. 14, 2017. 5 pages.

English translation of Office Action mailed Nov. 3, 2021 in CN Patent Application No. 201980023755.4. 5 pages.

English translation of Office Action mailed Nov. 26, 2021 in CN Patent Application No. 201980023904.7. 5 pages.

Communication pursuant to Article 94(3) EPC dated Jan. 31, 2022 in EP Patent Application No. 19708889.1. 6 pages.

Communication pursuant to Article 94(3) EPC dated Jul. 20, 2022 in EP Patent Application No. 19708889.1. 5 pages.

English translation of Office Action mailed Aug. 18, 2022 in CN Patent Application No. 201980023904.7. 7 pages.

Non-Final Office Action dated Aug. 25, 2022 in U.S. Appl. No. 16/984,955, filed Aug. 4, 2020. 18 pages.

Lake, Melinda A. et al.; "Microfluidic device design, fabrication, and testing protocols"; Protocol Exchange; Jul. 2015; DOI:10.1038/protex.2015.069; 27 pages.

Van Kooten, Xander F. et al.; "Passive removal of immiscible spacers from segmented flows in a microfluidic probe"; Applied Physics Letters; 106, 074102; 2015; 6 pages.

Tesar, Vaclav et al.; "Pneumatic sensors based on colliding curved wall jets"; Sensors and Actuators A: Physical; vol. 228; 2015; pp. 82-94.

Non-Final Office Action mailed Aug. 29, 2023 in U.S. Appl. No. 16/984,955, filed Aug. 4, 2020. 17 pages.

Communication pursuant to Article 94(3) EPC dated Feb. 21, 2023 in EP Patent Application No. 19708889.1. 8 pages.

English translation of Office Action mailed Feb. 27, 2023 in CN Patent Application No. 201980023904.7. 7 pages.

Final Office Action mailed Apr. 7, 2023 in U.S. Appl. No. 16/984,955, filed Aug. 4, 2020. 18 pages.

Notice of Allowance mailed Feb. 7, 2024 in U.S. Appl. No. 16/984,955, filed Aug. 4, 2020. 16 pages.

* cited by examiner

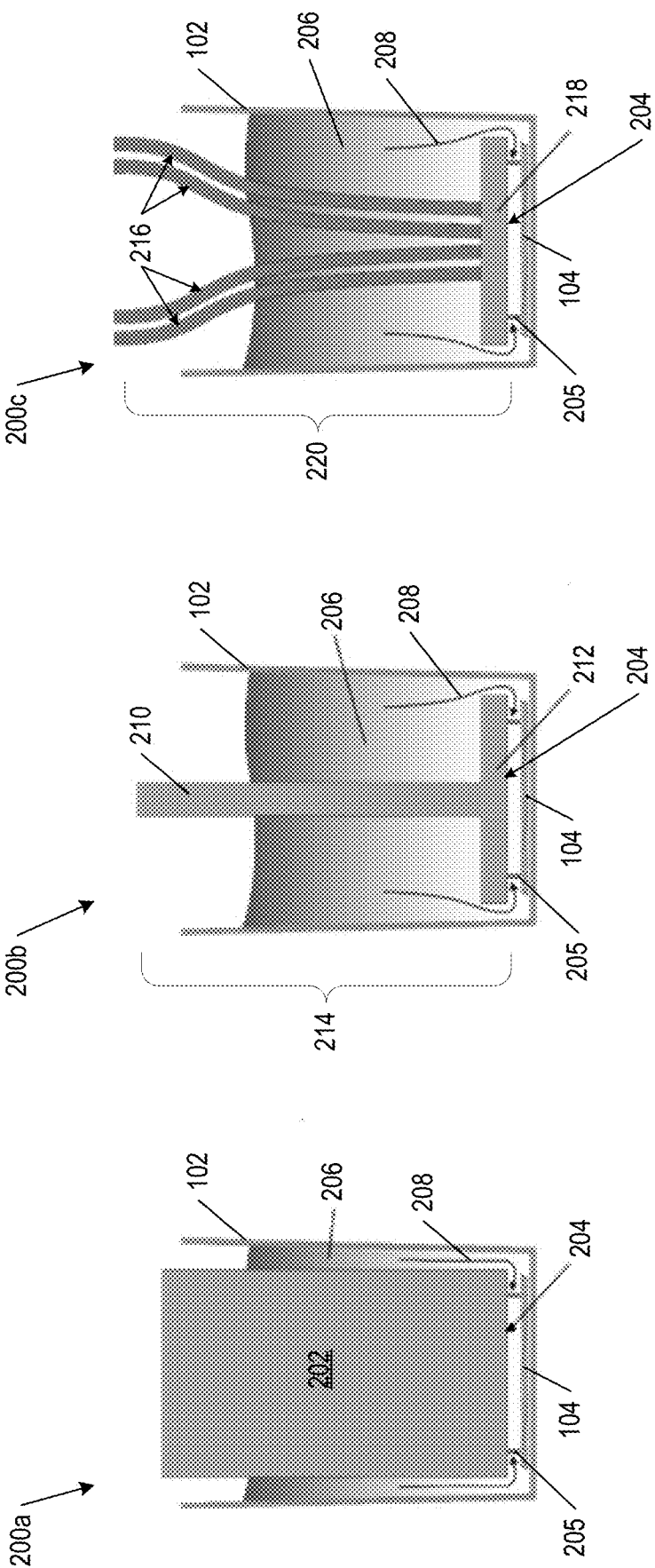

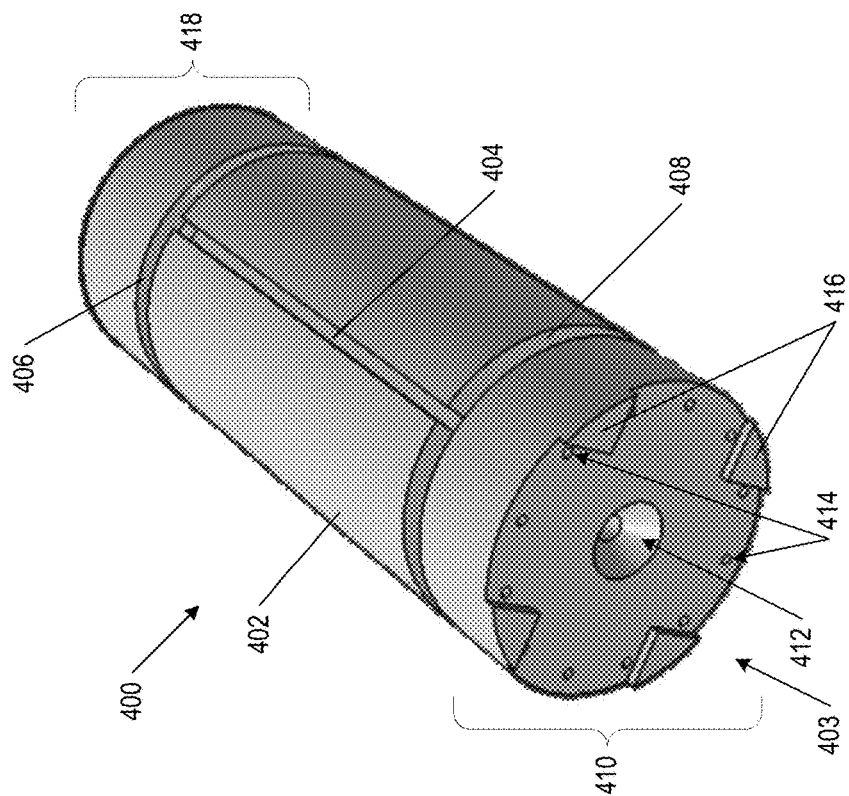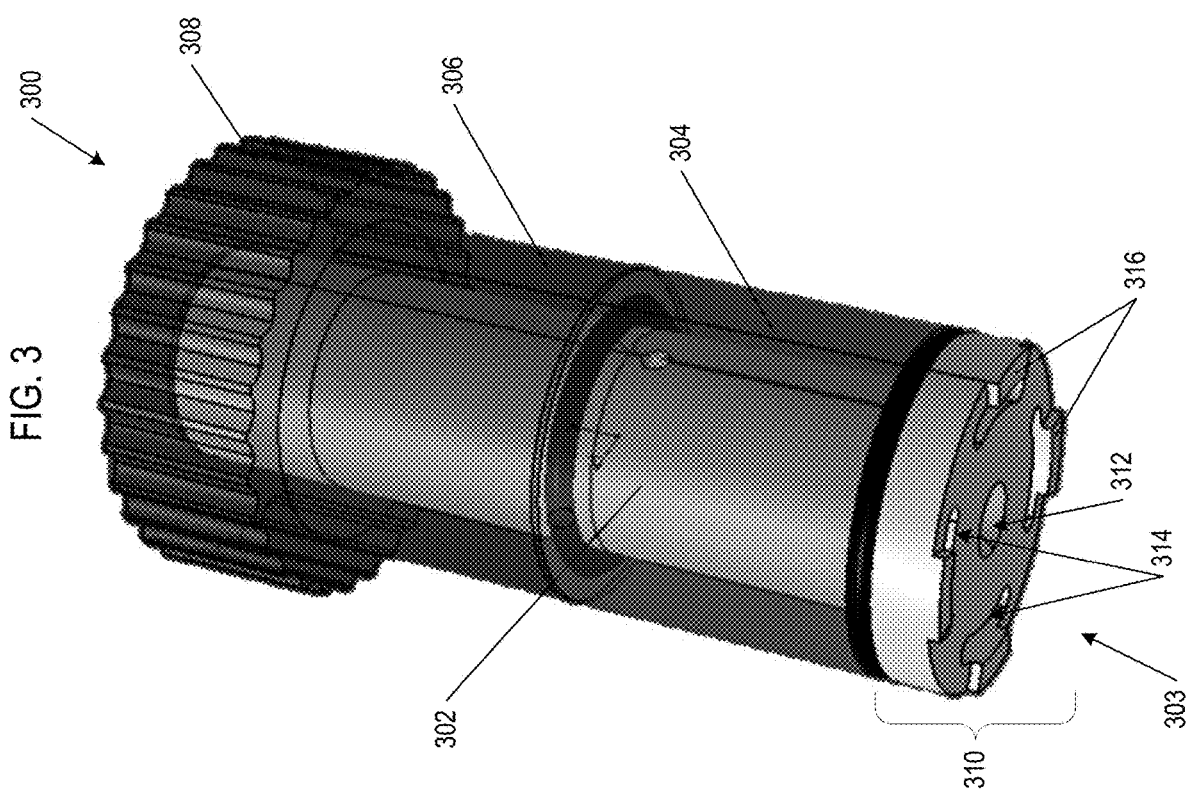

MICROFLUIDIC PROBE HEAD WITH ASPIRATION POSTS

CROSS-REFERENCE TO RELATED APPLICATIONS

This application is a continuation application of International Patent Application No. PCT/M2019/000007 entitled "MICROFLUIDIC PROBE HEAD WITH ASPIRATION POSTS," filed on Feb. 5, 2019, which claims priority to U.S. Provisional Patent Application No. 62/626,606, filed on Feb. 5, 2018; and is related to International Patent Application No. PCT/EP2019/052743, entitled "MICROFLUIDIC PROBE HEAD WITH BARRIER PROJECTIONS", filed concurrently on Feb. 5, 2019, the disclosures of which are hereby incorporated by reference in their entirety for all purposes.

TECHNICAL FIELD

The disclosure relates in general to the field of fluidic probe heads, devices that implement fluidic probe heads, and related methods of operation. In particular, it is directed to an microfluidic probe head designed for cell deposition.

BACKGROUND

Microfluidics deals with the behavior, precise control and manipulation of small volumes of fluids. The term microfluidics is sometimes colloquially used with reference to volumes across several orders of magnitudes (e.g., from milliliter volumes down to nanoliter volumes). There are some characteristics of fluid flow that are often constrained to micrometer-length scale channels and to volumes typically in the sub-milliliter range, but can also be observed with respect to millimeter-length scale channels and milliliter volumes of fluid. Some features of microfluidics originate through the behavior that liquids exhibit at the millimeter length scale, the micrometer length scale, or shorter. The flow of liquids in microfluidics is typically laminar. Volumes well below one nanoliter can be reached by fabricating structures with lateral dimensions in the micrometer range. Microfluidic devices generally refer to microfabricated devices, which are used for pumping, sampling, mixing, analyzing, and dosing liquids, often (but not exclusively) at such sub-milliliter volumes. A microfluidic probe is a device for depositing, retrieving, transporting, delivering, and/or removing liquids, in particular liquids containing chemical and/or biochemical substances. For example, microfluidic probes can be used in the fields of diagnostic medicine, pathology, pharmacology and various branches of analytical chemistry. Microfluidic probes can also be used for performing molecular biology procedures for enzymatic analysis, ribonucleic acid (RNA) and/or deoxyribonucleic acid (DNA) analysis, and proteomics.

With specific regard to microtiter plates, performing local chemical alterations, sequentially, on the bottom surfaces of wells in microtiter plates is very challenging. Implementing such processes of sequential chemistry conventionally requires relatively large volumes of processing liquid (in the range of tens of milliliters), and also often requires flushing relatively large volumes of liquid to reduce contamination between consecutive liquids. In many conventional protocols, the techniques include drying out the entire microtiter plate; however, drying the microtiter plate is not always an available option for avoiding contamination, given the stage or processing for various applications.

Depositing cells in a homogeneous, rapid and specific manner at defined locations on a surface is particularly challenging, especially when willing to deposit cells on standard substrates in biology, such as glass slides, Petri dishes, and microtiter plates. An additional challenge involves microfluidic probe heads that are designed to be used for horizontal scanning, which are generally not compatible with individual wells of microtiter plates, often being too wide, too large, with too broad a liquid dispensing area, or a combination thereof. Vertical variants microfluidic probe heads have been made to be relatively slender so as to fit within the well of a microtiter plate. However, the flow confinement sizes achieved by such vertical variants are generally not compatible with the patterns on the surface of the heads, and are unable to implement multiplexed tests. Moreover, the operation of a vertical microfluidic probe head tends to require operation at low fluid pressures to ensure desired deposition interaction, but it is difficult to control pressure in such heads with generally available pumps. Further, the design of many microfluidic probe heads is still directed toward a (very time consuming) scanning process, and it is particularly challenging to change direction while scanning with a vertical variant, as changes in direction can disrupt a hydrodynamic flow confinement area. Moreover, the vertical variant makes microtiter well processes highly challenging, since processing within microtiter plate sample wells generally requires maintaining a fixed distance to the surface, where the surface in many cases is a membrane, which is not conformal. Many such microfluidic probe heads also require extensive washing procedures during their operation.

BRIEF SUMMARY

The following presents a simplified summary of some embodiments of the disclosure in order to provide a basic understanding of the disclosure. This summary is not an extensive overview of the disclosure. It is not intended to identify key or critical elements of the disclosure or to delineate the scope of the disclosure. Its sole purpose is to present some embodiments and aspects of the disclosure in a simplified form as a prelude to the more detailed description that is presented later.

Generally, the present disclosure is directed to a microfluidic probe head that includes: a processing surface located at one end of the microfluidic probe head, configured to hydrodynamically confine fluids within a processing region proximate to the processing surface; one or more injection apertures in the processing surface; one or more aspiration apertures in the processing surface; and two or more posts extending outward from the processing surface, configured to establish a height of the processing region.

In some embodiments, the microfluidic probe head processing surface can have three injection apertures arranged in a triangular configuration. In some aspects, the three injection apertures can be spaced apart from each other such that, the processing region includes a stagnation space formed between the three injection apertures. In other aspects, the three injection apertures can be each connected to different fluid sources. In other embodiments, the microfluidic probe head processing surface can have four injection apertures arranged in a square or rectangular configuration. In some aspects, the four injection apertures are spaced apart from each other such that, the processing region includes a stagnation space formed between the four injection apertures. In further aspects, two or more of four injection apertures can be connected to different fluid sources.

In other embodiments, the one or more aspiration apertures of the microfluidic probe head can be a plurality of circular holes, arrayed along the perimeter of the processing surface. In some aspects, the apertures can be rectangular holes, slits, or apertures with other shapes. In some aspects, the one or more aspiration apertures can located within a recess or groove formed within the processing head.

In some aspects, the posts projecting outward (downward) from the processing surface can extend about 0.1 mm outward from the processing surface. In other aspects, the processing surface can have four such posts, arranged equidistantly from each other around the perimeter of the processing surface. In such aspects, a plurality of aspiration apertures can be positioned or grouped in between the four posts, also being arranged around the perimeter of the processing surface. Yet further for such aspects, each of the four posts can paired with an aspiration aperture, that aperture being positioned adjacent to each post on a side of the post facing the one or more injection apertures (inward toward the center of the processing surface).

In some embodiments, the microfluidic probe head can further include a probe interface section at an end of the microfluidic probe head distal (opposite) from the processing surface, where the probe interface section has fluid contact ports configured to connect the microfluidic probe head with one or more fluid sources and/or a vacuum source. In some aspects, the probe interface section can include four fluid contact ports, where three of the four fluid contact ports are connected to one or more fluid source reservoirs for injection of fluids, and where the fourth of the four fluid contact port is connected to a vacuum source for aspiration of fluids.

With regard to a further aspect, the disclosure is embodied as a method of operating an microfluidic probe head according to any of the embodiments above. The method comprises: positioning the microfluidic probe head in proximity with a sample surface or substrate to be processed, so as for the processing surface of the head to face the sample surface. Then processing liquid is injected via the liquid injection aperture while liquid is aspirated from the aspiration aperture, to process the sample surface.

In some embodiments, the processing liquid is a heterogeneous suspension comprising cells, and processing liquid is injected so as to deposit cells of the heterogeneous suspension onto the sample surface.

In some implementations, particularly with sample wells as the sample surface, the sample surface is first immersed in an immersion liquid. Thus, the microfluidic probe head will be at least partly immersed in the immersion liquid, when positioning it above the sample surface. In operation, the one or more additional apertures of the head can be used to inject or aspirate liquid, while otherwise aspirating liquid from the first aspiration aperture. In such embodiments, the steps of injecting the processing liquid and aspirating liquid are performed so as to maintain a hydrodynamic flow confinement of injected liquid between the injection aperture and the aspiration aperture.

Devices and methods embodying the present disclosure will now be described, by way of non-limiting examples, and in reference to the accompanying drawings. Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

BRIEF DESCRIPTION OF THE DRAWINGS

Illustrative aspects and embodiments are described in detail below with reference to the following drawing figures.

FIG. 2A illustrates a microfluidic probe configured for the deposition and aspiration of controlled volumes of fluids within a sample well, according to embodiments of the disclosure.

FIG. 2B illustrates a microfluidic probe configured for the deposition and aspiration of controlled volumes of fluids within a sample well, according to embodiments of the disclosure.

FIG. 2C illustrates a microfluidic probe configured for the deposition and aspiration of controlled volumes of fluids within a sample well, according to embodiments of the disclosure.

FIG. 3 illustrates the structure, housing, and processing surface for a microfluidic probe and probe head with aspiration posts, according to embodiments of the disclosure.

FIG. 4 illustrates the structure for a microfluidic probe and probe head and processing surface for a microfluidic probe head with aspiration posts, according to embodiments of the disclosure.

Figure 1:
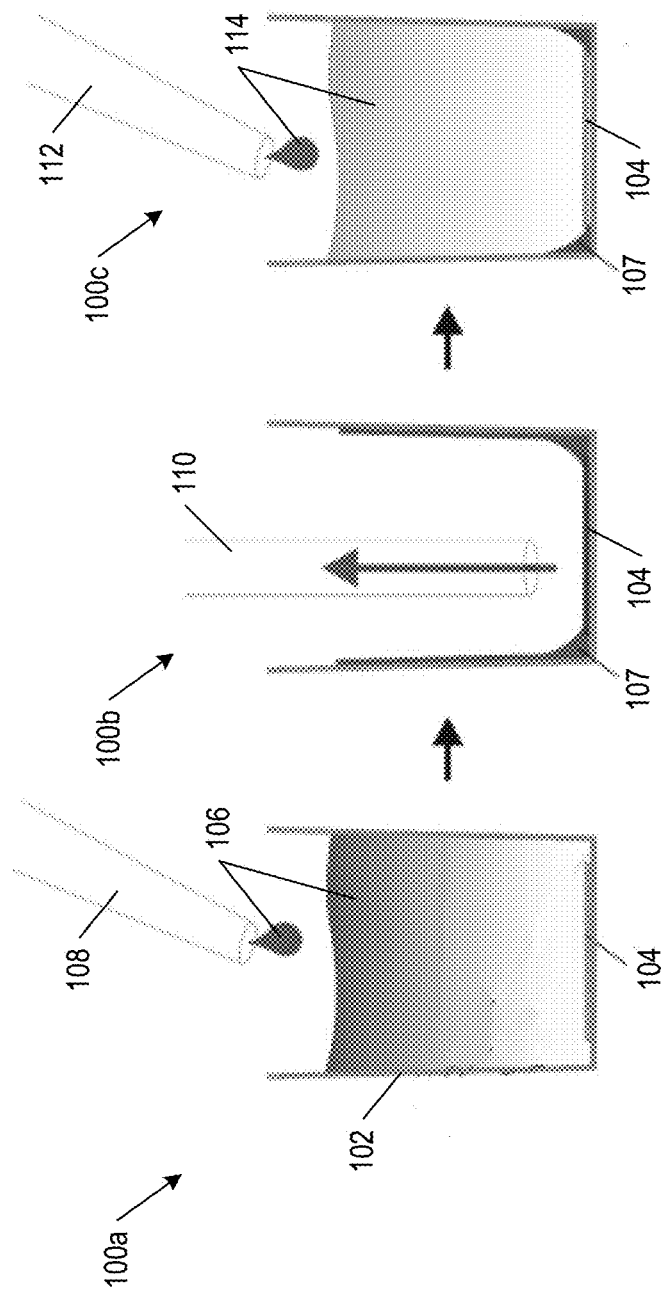
FIG. 1 illustrates a sequence of sample deposition and aspiration, as known in the art.

The accompanying drawings show simplified representations of devices or parts thereof, as involved in embodiments. Technical features depicted in the drawings are not necessarily to scale. Similar or functionally similar elements in the figures have been allocated the same numeral references, unless otherwise indicated.

DETAILED DESCRIPTION

Throughout this description for the purposes of explanation, numerous specific details are set forth in order to provide a thorough understanding of the many embodiments disclosed herein. It will be apparent, however, to one skilled in the art that the many embodiments may be practiced without some of these specific details. In other instances, well-known structures and devices are shown in diagram or schematic form to avoid obscuring the underlying principles of the described embodiments.

The systems and methods described herein facilitate the automation of fluid sample analysis, with applications in immunohematology, regenerative medicine and toxicology studies. Further, devices and methods as described here in can perform local and precise biochemical alterations on the surface of each single well in a microtiter plate while generally avoiding mixing with residual amounts of solutions when different liquids are introduced. This makes the techniques and disclosure disclosed herein particularly useful, for example, for antigen typing assays and antibody screening assays.

Some techniques of immunohematology testing involve "scanning" a blood sample across a broad array of reactants (horizontally, across the X-Y axes of a sample surface), which carries some inherent risk of signal mixing, cross-contamination, and the like. Earlier attempts to use microfluidics employed channels exposed on a fluidic head, but these lacked the hydrodynamic fluid control of the present disclosure.

A further application of microfluidics is testing within microtiter plates with minimal volumes of sample or other fluids. Such testing does not require movement along an X-Y axes while concurrently depositing processing fluid. Traditional heads used for such testing, however, are ill-suited to use with sample wells, at least because the shapes and sizes of fluidic probe heads used for that testing are too large, too wide, and/or too irregularly shaped to efficiently work with sample wells of microtiter plates. Microfluidic probe ("MFP") heads such as the ones disclosed herein, moving vertically (along the Z axis) into and out of sample wells of microtiter plates can provide advantages in that, due to the hydrodynamic flow confinement provided by the processing surfaces and mesas of the MFP heads, less volumes of fluid are needed to perform testing, the sample wells are easier to clean, the samples are more completely immersed in fluid, and contact between cells within a sample fluid and the receiving surface is increased.

In microtiter plate applications, the amount of processing fluids and rinsing fluids to achieve the desired chemistry, reactions, and cleaning is reduced relative to traditional sample well chemistry in such microtiter plates. The reduced amount of fluids is both more efficient and easier to process in that the volumes of fluid are smaller and the MFP heads can more precisely aspirate and/or rinse edges, corners, and walls of a sample well than traditional cleaning procedures. The control of fluid by hydrodynamic flow confinement ("HFC") also allows for sequential chemistry reactions to be performed within the same sample well, with the injection of processing fluids having samples and/or reagents alternating with injection of buffer or rising fluids. The HFC of the MFP head provides for sequential reactions (e.g. anti-body screening assays) to be carried out within the same sample well without significant concern for cross-contamination or other such errors, due to the alternating rinsing and overall control of the fluids beneath the processing surface of the MFP head.

Generally speaking, HFC relates to a laminar flow of liquid, which is spatially confined within an environmental liquid (alternatively referred to as an immersion liquid). In particular, aspiration apertures, optionally in combination with mechanical or liquid barrier elements, set the boundaries of HFC for a given MFP head and maintain desired flow characteristics of the injected processing liquid(s) within or underneath a specific region of an MFP head. Some embodiments and aspects of the present disclosure advantageously rely on hydrodynamic flow confinement as further described herein.

Devices and systems as considered herein can include other structures or means as are usual in microfluidics (e.g., tubing ports, valves, pumping means, vacuum sources) and can be configured to provide for HFC of the processing liquid(s) injected through the injection aperture(s). It can be understood that the MFP head and HFC of the present disclosure can be implemented in various embodiment of fluid handling systems capable of performing a wide range of chemistries on or within various plate, wells, slides, or the like. The MFP heads and their processing surfaces can be constructed or formed from generally biocompatible materials including, but not limited to, ceramics, plastics, polymers, glass, silicon, metals (e.g. aluminum, stainless steel, etc.), alloys, or combinations thereof. In several aspects, the MFP head can be fabricated from aluminum using lathe, milling, and/or etching techniques.

Embodiments and aspects of the present devices and methods allow cells to be deposited in a homogeneous, rapid, and specific manner on a substrate (or other such sample surface), at defined locations, from a heterogeneous suspension. The present approach eases the deposition of cells on standard substrates, such as glass slides, Petri dishes, and microtiter plates (e.g. microplates with 6, 24, or 96 wells). The MFP head can be moved horizontally or vertically, or both, as appropriate for controlling fluid flow and/or vacuum at the processing surface, such that the MFP head can move as appropriate for deposition and aspiration at, on, or along the corresponding substrate.

Generally, in embodiments of the present microfluidic probe and microfluidic probe heads, the average diameter of any given injection aperture (measured either at the processing surface of the probe head or at an inner diameter further up into the body of the probe) can be between 100 μm and 500 μm, and can be a diameter at any increment, gradient, or range therein. For example, the average diameter of an injection aperture can be approximately 300 μm±50 μm. Further, notwithstanding the depictions in the accompanying drawings, an injection aperture need not necessarily be a rounded hole, for example, an injection aperture may have a square, rectangular, triangular, or notched shape. The average width of aspiration apertures disclosed herein can be between 20 μm and 100 μm, and can be at any increment, gradient, or range therein. The minimum distance between the injection apertures and aspiration apertures can vary based on the particular design and parameters needed for hydrodynamic control between a processing surface and a substrate.

The size and relative location of injection apertures and aspiration apertures as considered in the exemplary embodiments herein are configured to maintain hydrodynamic flow control. There is a limit to the size and scaling of such microfluidic probe heads, which can be based on the hydrodynamic resistance at the apex of the processing surface and the side walls of the sample well, and/or the spacing of the apertures from the bottom of the sample well. In particular, the ratio of the hydrodynamic resistance between the apex of the probe head processing surface to the resistance of sample well side-wall should be in the range of from 0.90 to 0.98. As can be understood from this ratio, the hydrodynamic resistance between the apex of the gap over the substrate or sample surface should not be lower than the flow resistance in the area where the immersion liquid is supplied (which for a sample well, is from the side walls to the bottom of the sample well). In other words, fluid flow should be generally directed radially outward, and the hydrodynamic resistance between the apex of the probe head processing surface should be greater than resistance at the sides of an MFP head and sample well wall such that fluid does not significantly flow inward back to one or more centrally located injection apertures.

Further, the spacing of MFP head during operation within microtiter plates wells can be proportional to the relationship between sizes of the MFP head and the sample well in which it is disposed. For example, in some embodiments, the distance of aspiration apertures from the outer edge (perimeter) of the processing surface of an MFP head can be configured to be from 10% to 20% of the diameter of the sample well in which the MFP head is designed to operate. The distance of the aspiration apertures from the edge of a respective MFP head can be varied as appropriate to the application for which the MFP head will be used. Accordingly, in other embodiments, the distance of aspiration apertures from the outer edge of the MFP head can be configured to be about 80% the diameter of the sample well in which the MFP head is designed to operate. Further embodiments provide for aspiration apertures that can be positioned, from the edge of their respective MFP head processing surface, a distance that is from about 10% to about 80% of the diameter of a sample well in which the MFP head is designed to operate. This specific positioning of aspiration apertures relative to a component (e.g. a microtiter plate) separate from the MFP head accommodates for control of resistance and fluid flow as appropriate for a particular implementation.

The variations of the MFP heads discussed in detail below include processing surfaces that have one or more aspiration apertures (which can be circular, oblong, curved, square, rectangular, otherwise shaped) that are arranged to at a perimeter around an injection aperture (or injection apertures) such that the flow of injected fluid is effectively surrounded by a vacuum or fluid draw. Due to the arrangement of aspiration apertures around the injection aperture, a degree of confinement of the injected liquid can be obtained during operation of the MFP head. Specifically, injected liquid remains confined within the desired area underneath the MFP head due to presence of liquid aspirated at the aspiration apertures, which in part due to the flow and turbulence at the zone of aspiration, forms a barrier extending around the injected liquid. This barrier created by the liquid aspiration helps to improve homogeneity in the deposited liquid (or particles thereof, such as cells). Further, the arrangement of the aspiration apertures allows for environmental or immersion liquid in the vicinity of the MFP head to be aspirated at the same perimeter via the aspiration apertures during operation of the MFP head. This allows the flow velocity of the injected liquid to be set partly (if not essentially) independent from the aspiration flow, which, in turn, eases the operation of the head.

Further variations of the MFP head and processing surfaces considered below can include alternative or additional mechanical barriers, such as a solid structure that extends from the processing surface, affecting the flow and direction of the injected liquid having sample or cells of interest. Such solid barriers positioned between the injection and an aspiration apertures guide, push, or pinch the injected fluid such that the injected fluid can improve and even maximize contact with an underlying sample surface (e.g., glass slides, Petri dish, microtiter plates or wells, etc.) thereby improving deposition, bonding, or interaction of cells in the injected fluid with the sample surface.

In many embodiments, the microfluidic probe head can have n liquid aspiration apertures (e.g. holes, slits, etc.) on the processing surface ($n \geq 2$). The n aspiration apertures can be arranged to have rotational symmetry of order n on the processing surface. The gaps between neighboring aspiration apertures are symmetrically distributed, so as to lower the influence of any given scanning direction or flow variance on deposited material. Each of the aspiration apertures can, for instance, be positioned along the circumference of a same circle on the processing surface, and can be relatively close to the perimeter of the processing surface. Similarly, in other embodiments, the MFP head can have more than one injection aperture, where those injection apertures have can be arranged to have rotational symmetry on the processing surface.

For applications using an MFP head for conducting chemistry within sample wells of a titer plate, the size and positioning of the MFP head within each well is often critical. If the MFP head is not substantively smaller in diameter than the well, a non-centered position can cause the MFP head to be too close to a side wall of the well, or even contact a side wall, and thus cause irregular flow of the processing and immersion liquid. Conversely, if the MFP head too small (relatively) to the size of the sample well, or has the injection aperture and/or aspiration apertures not centered, the MFP head will require more extensive work to be positioned properly for best processing over the area of interest. Accordingly, providing a device that the device is self-aligning/self-positioning as the deice approaches the microtiter plate is preferable. In this sense, self-alignment refers to both X-, Y-, and Z-axis alignment, as well as self-adjusting the possible tilt variations. Self-alignment can be achieved by adding mechanical features, such as posts, clamps, rotational joints, soft "cushioning" materials, springs, or even air bearings of hydrodynamic levitation, etc.

In the context of the present disclosure, posts arranged to extend or protrude from the processing surface of an MFP head are used, in part, to self-align the MFP head. These posts are generally proximate to aspiration apertures in the processing surface, and/or at an equal radial distance along with the aspiration apertures from the center of the processing surface. In some embodiments, these posts are flush with or immediately adjacent to aspiration apertures. Accordingly, these structures are referred to in the present disclosure as aspiration posts. These posts are also distinct from the mechanical barriers for controlling fluid flow described herein. The posts extend outward from the processing surface of the MFP head, in a direction parallel with the longitudinal axis of the MFP head. In other words, when in an operational position, the posts are viewed as extending downward toward a surface. In many embodiments, the posts do not extend in a radial direction from the center of the processing surface; however, in alternative embodiments, the posts can extend semi-diagonally, both downward and radially outward from the MFP head.

The aspiration posts can contribute several advantages to MFP heads. In operation, the aspiration posts can touchdown onto the surface or substrate below the processing surface. The aspiration posts thereby mechanically determine the distance of the apex of the processing surface to the underlying substrate or sample surface. In other words, the height of the aspiration posts (or other analogous features) determines the gap distance between the processing surface (and thus the injection and aspiration apertures) and the sample substrate, in effect establishing the height and operational space of the processing region. Thus the height of the aspiration posts can be tuned or configured to provide for a specific or desired injection/aspiration fluid flow geometry. The height of the aspiration posts can also guide the design of the injection and/or aspiration apertures; for example, relatively high or tall aspiration posts would necessitate relatively smaller injection apertures (with corresponding higher fluid injection pressure) so that the processing liquid could reach the underlying surface substrate.

Aspiration posts can also create tension on the substrate membrane below the processing surface, and therefore minimize topographical variations of the underlying substrate/surface. Touch-down mode can also be interpreted as a mechanical feature, keeping the apex at a given distance to the surface. The location of aspiration posts on the processing surface can vary. For example, aspiration posts can be located along one edge of the processing surface, and thus contact only the corresponding edge of the of the substrate within the titerplate and/or titerplate well. It can be understood that placement of the aspiration apertures in relation to the edges of the device and the injection aperture can function to ensure that that no injected processing liquid reaches the areas which are not be to be processed (e.g. corners and side walls of a sample well). The geometry and arrangement of the aspiration apertures, individually or in combination with the aspiration posts, plays a key role in proper functioning of the MFP heads considered herein.

As used herein, unless otherwise indicated, the term "microfluidic" refers to the handling of fluid volumes that deal with the behavior, precise control, and manipulation of small volumes of fluids, ranging from milliliter volumes to nanoliter volumes, and increments and gradients of volume therein. Accordingly, "microfluidic probe heads" (MFP heads) generally refer to probe heads that are part of miniaturized fluid-transport systems and devices, capable of handling and processing fluid volumes ranging from milliliter volumes to nanoliter volumes, and increments and gradients of volume therein. Where specifically indicated, certain implementations of microfluidic devices and/or probe heads are constrained to micrometer-length scale channels and to volumes typically in the sub-milliliter range.

As used herein, unless otherwise indicated, the term "mesa" generally refers to the portions of the processing surface of an microfluidic probe head, inclusive of (but not limited to) the apertures for aspiration, apertures for deposition, apertures for contour and mesa shape control, barriers, contours, step-features, rounded corners, recesses, reliefs, grooves, and other such structural aspects that forms a processing surface for the fluidic head.

As used herein, unless otherwise indicated, the terms "upper" and "lower" generally refer to the orientation of a microfluidic probe as viewed during operation, where the lower portion of a microfluidic probe, particularly the probe head, is proximate to a substrate or sample surface (e.g. the bottom of a sample well), and where the upper portion of a microfluidic probe, particularly the probe interface section, is distal from a substrate or sample surface and is rather the point of physical contact between any given microfluidic probe and the overall fluid handling system to which the microfluidic probe is connected.

As used herein, unless otherwise indicated, the term "about" is used to provide flexibility to a numerical range endpoint by providing that a given value may be greater than or less than the indicated value. In particular, the given value modified by about may be at or within ±10% from that value.

As used in this specification and the appended claims, the singular forms "a", "an", and "the" include plural referents unless the content clearly dictates otherwise. Thus, for example, reference to a system comprising "a binding agent" includes system comprising one or more binding agents. Likewise, reference to "a substance" includes one or more substances.

FIG. 1 shows a progression of fluid deposition, aspiration, and second fluid deposition as known in the field. At step 100a, a sample well 102 holding a substrate 104 is filled with first fluid 106, where first fluid 106 is deposited with first dispenser 108 (e.g. a pipette or the like). Substrate 104 can have any variety of binding sites, reagents, fixed samples, or the like. First fluid 106 can have any variety of sample material, such as cells, antibodies, small molecules, or the like. At step 100b, first fluid 106 is aspirated out of sample well 102 via aspirator 110, with the assumption that any amount of intended and desired reaction between substrate 104 and first fluid 106 has been completed. However, residual material 107 (e.g., salts, cells, detritus, etc. from first fluid 106) remain within the corners of the sample well 102. The residual material 107 remains in or on the corners, edges, and crevices of the sample well 102 in part due to the physical limitations of the aspirator 110 (e.g., being too large to adjust angle within the sample well 102) and the limitations of the draw or vacuum applied within the sample well 102 through the aspirator 110. Traditional procedures provide for no good way to ensure uniform liquid flow in these sample well 102 corners and side walls. The residual material 107 thus becomes a cross-contamination source, as seen in step 100c where second dispenser 112 deposits second fluid 114 into the sample well 102. Second fluid 114 can be a washing or rinsing fluid such as a buffer, or second fluid 114 can be also be a fluid having any variety of sample material, such as cells, antibodies, small molecules, or the like. Residual material 107 can cause a rinsing action to displace the sample material from first fluid 106 in a manner that is not desired during step 100c. Residual material 107 can also cause for the confusion of signals when mixed with any sample contained in second fluid 114 that binds or reacts with substrate 104. Traditional procedures to reduce the cross-contamination inherent in these methods, such as almost complete drying or elaborate and extensive rinsing/purging of buffer liquids, are imperfect.

FIGS. 2A, 2B, and 2C each illustrate variations of exemplary microfluidic probe heads configured for the deposition and aspiration of controlled volumes of fluids within a sample well. In particular, FIG. 2A shows a first arrangement 200a of a first microfluidic probe 202 within a sample well 102, FIG. 2B shows a second arrangement 200b of a second microfluidic probe 214 within a sample well 102, and FIG. 2C shows a third arrangement 200c of a third microfluidic probe 220 within a sample well 102. In many aspects, the fluids injected or deposited can include chemical reagents and compounds, and can also be a non-Euclidian fluid and/or include cells. Accordingly, each of these arrangements allows for systems and devices where sequential chemistry can be performed within the sample well 102 with a minimum of cross-contamination concern, due in part to the hydrodynamic flow confinement (HFC) provided by the processing surface 204 of each probe head in relation to a substrate 104 at the bottom of the sample well 102.

In some implementations, the microfluidic probes have aspiration posts 205 extending downward from the processing surface 204, making contact with regions of either the substrate 104 or the bottom of the sample well 102. The aspiration posts 205 can be optional structures protruding from the processing surface 204, but when present, can provide for specific advantages. In one aspect, the aspiration posts 205 help to maintain a consistent and even operational distance between the substrate 104 and the processing surface 204. In another aspect, the aspiration posts 205 can apply pressure to the perimeter of the substrate 104, helping to maintain tension on or the shape (e.g., planar and/or convex) of the substrate 104. The length (or depth) of the aspiration posts 205 can vary depending on the structures of the microfluidic probe 202 and processing surface 204 from which said aspiration posts 205 extend.

FIG. 2A shows the first arrangement 200a using the first microfluidic probe 202, located at an operation position within the sample well 102, proximate to the substrate 104. Both the first microfluidic probe 202, specifically the processing surface 204 of the first microfluidic probe 202, and the substrate 104 are shown immersed in processing fluid 206. First microfluidic probe 202 has injection apertures and aspiration apertures within the processing surface 204 leading into fluid channels within the body of the first microfluidic probe 202, connected to reservoir sources of other fluids (e.g., sample fluids, reagents, buffers, etc.) and/or waste or alternative collection reservoirs, respectively. When the first microfluidic probe 202 (and its respective processing surface 204) is at an operating position proximate to a substrate 104, aspirators around the perimeter of the processing surface 204 can draw up fluid such that a fluidic barrier is formed between a central region of the processing surface 204 and the remainder of the sample well 102 volume. A fluidic barrier, in the context of the present disclosure, is a region of fluid flow where aspiration and/or the shape of the proximate structures form an eddy or fluid turbulence such that the fluid flow stays within a defined and desired region, and thereby contributes to the HFC of a microfluidic probe head. Ambient flow 208 shows a portion of the draw of such aspirators, where processing fluid 206 is pulled into the first microfluidic probe 202 and does not reach the central portion of volume between the processing surface 204 and the substrate 104.

FIG. 2A also represents a variation of the disclosed system, showing that the first arrangement 200a minimizes the volume of processing fluid 206 needed within the sample well 102 because the first microfluidic probe 202 occupies a significant portion of that space. Further, first microfluidic probe 202, when at an operating position within a sample well 102, can be 100 µm above the substrate 104, being equal to the height of the aspiration posts 205. In other aspects, aspiration posts 205 extending from the bottom of the first microfluidic probe 202 can set the distance between the first microfluidic probe 202 and the substrate 104 to be greater or less than 100 µm.

FIG. 2B shows the second arrangement 200b using the second microfluidic probe 214 (having a "nail" shape), located at an operation position within the sample well 102, proximate to the substrate 104. The second microfluidic probe 214 can be formed of a probe stem 210 and a probe head 212. Both the second microfluidic probe 214, specifically the processing surface 204 of the second microfluidic probe 214, and the substrate 104 are shown immersed in processing fluid 206. Second microfluidic probe 214 has injection apertures and aspiration apertures within the processing surface 204 leading into fluid channels within the probe stem 210, connected to reservoir sources of other fluids (e.g., sample fluids, reagents, buffers, etc.) and/or waste or alternative collection reservoirs, respectively. When the second microfluidic probe 214 (and its respective processing surface 204) is at an operating position proximate to a substrate 104, aspirators around the perimeter of the processing surface 204 can draw up fluid such that a fluidic barrier is formed between a central region of the processing surface 204 and the remainder of the sample well 102 volume. Ambient flow 208 shows a portion of the draw of such aspirators, where processing fluid 206 is pulled into the second microfluidic probe 214 and does not reach the central portion of volume between the processing surface 204 and the substrate 104. As compared to the variation shown in FIG. 2A, the second microfluidic probe 214 can be used for applications to minimize the displacement of environmental immersion liquids and/or processing fluid 206.

Further, second microfluidic probe 214, when at an operating position within a sample well 102, can be 100 µm above the substrate 104. In other aspects, aspiration posts 205 extending from the bottom of the second microfluidic probe 214 can set the distance between the first microfluidic probe 202 and the substrate 104 to be greater or less than 100 µm. In some aspects, the probe head 212 can be from 100 µm to 300 thick µm, or can have a thickness proportional to the width or diameter of the probe stem. In some aspects, the probe head 212 can have a shape that is circular, square, or otherwise shaped to conform within the microplate well.

FIG. 2C shows the third arrangement 200c using the third microfluidic probe 220 (having a "multi-tube" configuration), located at an operation position within the sample well 102, proximate to the substrate 104. The third microfluidic probe 220 can be formed of probe tubing 216 and a probe plate 218. (In some aspects, probe plate 218 can be similar to probe head 212 from second microfluidic probe 214.) Both the third microfluidic probe 220, specifically the processing surface 204 of the third microfluidic probe 220, and the substrate 104 are shown immersed in processing fluid 206. Third microfluidic probe 220 has injection apertures and aspiration apertures within the processing surface 204 leading into probe tubing 216, connected to reservoir sources of other fluids (e.g., sample fluids, reagents, buffers, etc.) and/or waste or alternative collection reservoirs, respectively. When the third microfluidic probe 220 (and its respective processing surface 204) is at an operating position proximate to a substrate 104, aspirators around the perimeter of the processing surface 204 can draw up fluid such that a fluidic barrier is formed between a central region of the processing surface 204 and the remainder of the sample well 102 volume. Ambient flow 208 shows a portion of the draw of such aspirators, where processing fluid 206 is pulled into the third microfluidic probe 220 and does not reach the central portion of volume between the processing surface 204 and the substrate 104. As compared to the variation shown in FIG. 2A, and similarly to the variation of FIG. 2B, the third microfluidic probe 220 can be used for applications to minimize the displacement of environmental immersion liquids and/or processing fluid 206.

Further, third microfluidic probe 220, when at an operating position within a sample well 102, can be about 100 µm above the substrate 104. In some aspects, the probe plate 218 can be from 100 µm to 300 thick µm. In some aspects, the probe head 212 can have a shape that is circular, square, or otherwise shaped to conform within the microplate well. In further aspects, probe tubing 216 can be formed of tubes having a degree of compressibility and flexibility, such that third microfluidic probe 220 has a greater tolerance for motion or oscillation (intentional or inadvertent) of the underlying microplate.

FIGS. 2B and 2C also represent a variation of the disclosed system, showing that both the second arrangement 200*b* and the third arrangement 200*c* can accommodate a volume of processing fluid 206 that fills more than half of the space within sample well 102.

All of the embodiments shown by the microfluidic probes in FIGS. 2A, 2B, and 2C have processing surfaces that cover about 80% of the bottom of the sample well (and effectively all of the substrate supported by the bottom of the sample well), which establishes the area under hydrodynamic flow confinement.

It can be appreciated from FIGS. 2A, 2B, and 2C that the distance between a processing surface and an underlying substrate is an important variable to control in order to maintain HFC within the desired region during operation of the MFP head. This distance between the processing surface and the substrate can be referred to as a working distance. In various aspects, the working distance can be a predetermined height above the substrate, set according to the height of aspiration posts extending from the processing surface. In such aspects, the height of aspiration posts (and thus the working distance) can be set according to a calculated height, where the calculated height can be a proportion or ratio between the size or diameter of the sample well, the size or area of a target region on a sample surface or substrate, the size or diameter of the processing surface, the size or diameter of injection apertures in the processing surface, the size or diameter of aspiration apertures in the processing surface, the location of injection and aspiration apertures along the processing surface, or a combination thereof.

Moreover, the aspiration posts, being located at or proximate to the perimeter of the processing surface can apply or distribute pressure where the aspiration posts touch down on the corresponding perimeter of the underlying substrate. In many cases, the substrate situated on the bottom of a sample well will not be completely level or even, and in some cases the substrate may be partially warped. Such an uneven substrate can be detrimental to the intended binding and chemistry of an assay. A microfluidic probe with aspiration posts can at least partially even out the plane of the substrate surface, where the microfluidic probe is lowered into a sample well to a height where pressure is applied to the perimeter of the substrate through the aspiration posts. Evening out any unevenness in the substrate can further improve the HFC of the processing surface within the sample well.

FIG. 3 illustrates the structure, housing, and processing surface for an exemplary microfluidic probe 300 with aspiration posts. As shown, the probe core 302 is positioned within a lower housing 304 component and an upper housing component 306. In some aspects, the probe core 302 has fluidic channels that run within the body of the probe core 302, and also fluidic channels formed (e.g. cut, etched, molded, etc.) in the exterior surface of the probe core 302. Fluidic channels on or along the exterior surface of the probe core 302 can be covered with the lower housing 304 and upper housing 306 components to as to be a confined space through which fluid can flow. In some aspects, the lower housing 304 and upper housing 306 components can be a heat-shrinking tubing material that is fit and/or adhered around the probe core 302, closing or covering external channels in the surface of the probe core 302, thereby forming capillaries for fluid flow. In alternative aspects, the lower housing 304 and upper housing 306 components can be a single static piece fit and/or adhered around the probe core 302. A control gear 308 can be fit around one end of the probe core 302, specifically the end of the probe core 302 distal from the probe head 310. The tubing connector is positioned around the upper housing and can secure tubing from fluid sources to the microfluidic probe. The size of the tubing connector can accommodate the number of tubes that need to be connected, provide for larger fluid passages to help avoid bubble formation, and can be molded to be gripped and held within a larger overall instrument. In operation, the probe head 310 (and its processing surface 303) is the section of the probe 300 that is proximate to and/or in contact with a sample surface or substrate.

The size of the tubing connector 308 can accommodate the number of tubes that need to be connected, provide for larger fluid passages to help avoid bubble formation, and can be molded to be gripped and held within a larger overall instrument. In operation, the probe head 310 (and its processing surface 303) is the section of the probe 300 that is proximate to and/or in contact with a sample surface or substrate.

In some embodiments, the probe core 302, lower housing 304, and/or upper housing 306 can be made from milled or cast aluminum. In other embodiments probe core 302, lower housing 304, and/or upper housing 306 can be made from molded or 3D-printed plastics.

The processing surface 303 of the probe head can be formed to have apertures that connect with the fluidic channels of the probe core 302, and can further have aspiration posts 316 extending or projecting from the processing surface 303. In the embodiment shown in FIG. 3, an injection aperture 312 is located in the center of the processing surface 303 with four (4) aspiration apertures 314 located around or adjacent to the perimeter of the processing surface 303, generally equidistant from each other along the perimeter and each also equidistant from the injection aperture 312. The aspiration apertures 314 are each positioned next to aspiration posts 316, and in the embodiment shown, the interior facing wall of each aspiration post 316 is flush with a corresponding fluidic channel surface that a respective aspiration aperture 314 open into. In other words, for the circular processing surface 303, the aspiration apertures 314 and aspiration posts 316 are located around the perimeter of the processing surface 303 at 90° increments. The injection aperture 312 can provide for an opening to the fluidic channels within the body of the probe core 302, while the aspiration apertures 314 can provide for openings to the fluidic channels formed in the exterior surface of the probe core 302 and covered by the lower housing 304 and/or upper housing 306 components. In all embodiments, lower housing 304 and upper housing 306 components should have a surface roughness (for the sides exposed to fluid) that does not exceed a value which could have a negative influence on the test or the fluidic behavior of the device (e.g. carry-over due to pores in the material).

FIG. 4 illustrates the structure for an exemplary microfluidic probe 400 and processing surface for a microfluidic probe head with aspiration posts. In this embodiment, microfluidic probe 400 is formed as a unitary component from a single piece. In some aspects, microfluidic probe 400 can be formed from aluminum or an aluminum alloy. Microfluidic probe 400 is shown without additional housing components, such as a polymer tube (applied by heat-shrinking) covering the microfluidic probe, allowing for further aspects of probe core 402 to be shown in detail. Microfluidic probe 400 is also shown from a perspective view that focuses on the processing surface 403. Probe core 402 includes external channel 404 formed in the exterior surface of probe core 402, running longitudinally along the probe core 402 portion of the microfluidic probe 400. (When covered by a polymer tube, external channel 404 is closed such that fluid does not spill out along its length.) FIG. 4 also shows two lateral grooves running around the circumference of the probe core 402, upper lateral groove 406 and lower lateral groove 408. Lower lateral groove 408 helps to define the region of the fluid probe 400 that forms the probe head 410. Similarly, upper lateral groove 406 helps to define the probe interface section 418, where the microfluidic probe 400 can be gripped, clamped, or held by a portion of an overall fluidic device. These fluidic channels in the microfluidic probe 400, external channel 404, upper lateral groove 406, and lower lateral groove 408 can all be in fluidic communication with each other and (when covered by one or more housing components) can allow for the passage of fluid along or through the microfluidic probe. In some aspects, external channel 404, upper lateral groove 406, and lower lateral groove 408 can each be about 0.2 mm deep, as measured relative to the exterior surface of the probe core 402.

The processing surface 403 of the probe head can be formed to have apertures that connect with the fluidic channels of the probe core 402, and can further have aspiration posts 416 extending or projecting from the processing surface 403. In the embodiment shown in FIG. 4, an injection aperture 412 is located in the center of the processing surface 403 with twelve (12) aspiration apertures 414 located around or adjacent to the perimeter of the processing surface 403, generally equidistant from the injection aperture 412. The aspiration apertures 414 are arranged in groups of three, in between aspiration posts 416, where there are four aspiration posts arranged equidistant from each other. In other words, for the circular processing surface 403, the aspiration posts 416 are located around the perimeter of the processing surface 403 at 90° increments. The injection aperture 412 can provide for an opening to the fluidic channels within the body of the probe core 402, while the aspiration apertures 414 can provide for openings to the fluidic channels (external channel 404, upper lateral groove 406, and lower lateral groove 408) formed in the exterior surface of the probe core 402. In some aspects, aspiration posts can extend about 0.1 mm outward from the plane defined by the processing surface 403. As noted above, in use a microfluidic probe 400 can be lowered to a height within a sample well such that the four corner aspiration posts 416 touch down and apply pressure on the outer edges of a substrate, flattening the substrate to be in a better configuration for conducting assay chemistry. In various aspects aspiration posts 416 can have a height of from thirty micro meters to two hundred micrometers (30 μm-200 μm), or any increment or gradient of length within that range.

Figure 5:
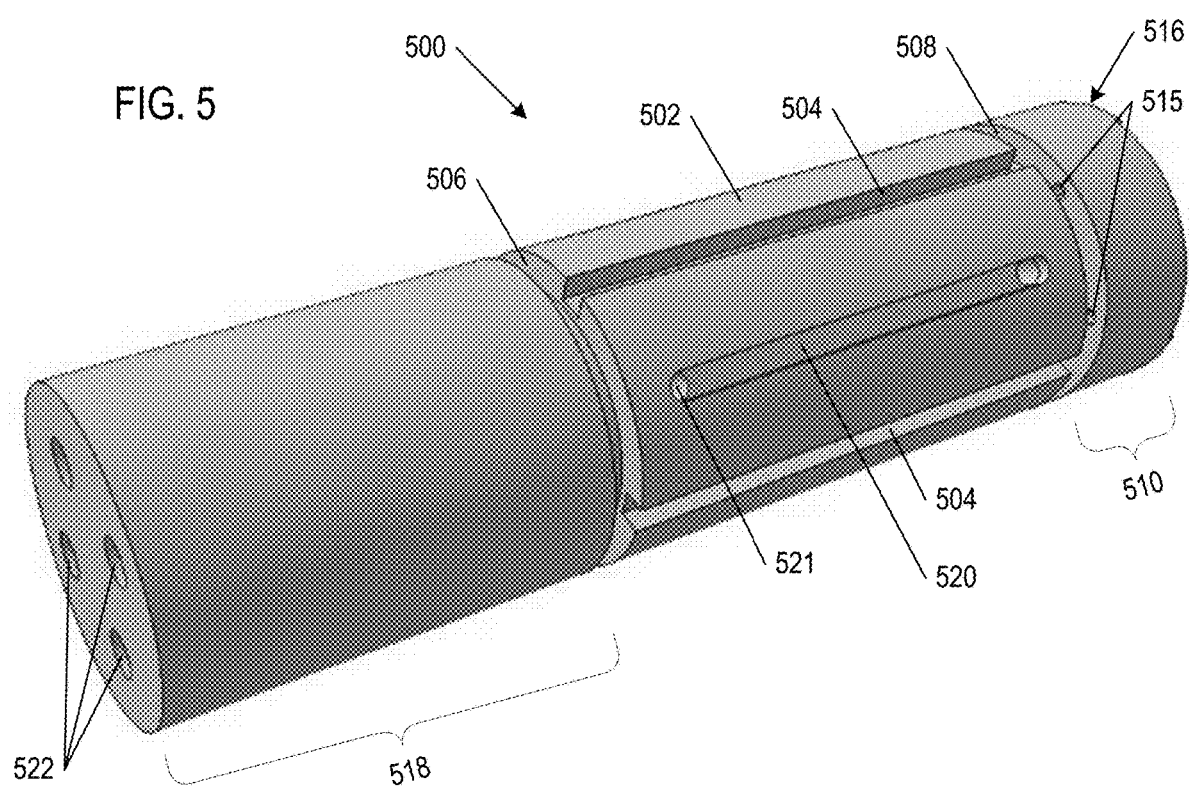
FIG. 5 illustrates the structure for a microfluidic probe with a source fluid connection configuration, according to embodiments of the disclosure.

FIG. 5 illustrates the structure for an exemplary microfluidic probe 500, focusing on the configuration for connection to a source fluid or reservoir. Probe core 502 is shown having exterior channels 504 formed in the exterior surface of probe core 502, running longitudinally along the probe core 502. Microfluidic probe 500 is shown from a perspective view that allows for illustration of fluid contact ports 522 within the probe interface section 518. The probe interface section 518 of microfluidic probe 500 is shown with four (4) fluid contact ports 522 in the uppermost surface of the microfluidic probe 500. Also seen in FIG. 5 are fluidic channels 515 that pass through probe head 510, which are generally used for aspiration, and lead into lower lateral groove 508. As in other variations, lower lateral groove 508, external channels 504, and upper lateral groove 506 are in fluidic communication with each other. Further, aspiration posts 516 along the perimeter or circumference of the probe head 510 are shown projecting outward from the processing surface of probe head 510, giving a relative sense of proportion between the height of the aspiration posts 516 as compared to the probe head 510 for the exemplary microfluidic probe 500. In various aspects aspiration posts 516 can have a height of from thirty micrometers to two hundred micrometers (30 μm-200 μm), or any increment or gradient of length within that range.

FIG. 5 also shows a variation of microfluidic probe 500 having a secondary longitudinal channel portion 520 running along the probe core 502, which is separate from the external channel 504. The secondary longitudinal channel portion 520 can be located in portions of the probe core 502 between the external channel 504, and in various aspects there can be one or more secondary longitudinal channel portions 520 formed in the probe core 502. The secondary longitudinal channel portion 520 has two probe body ports 521, located at the ends of secondary longitudinal channel portion 520 leading into fluidic channels in the body of the probe core 502. The fluidic channels within the body of the probe core can be used for the injection of a primary fluid (e.g. a processing fluid) or a supplemental fluid (e.g. buffer or rinsing fluid), or for aspiration of fluids. These fluidic channels can be routed through the secondary longitudinal channel portion 520 so as to give a path for egressing away from the microfluidic probe 500, for example out through surrounding housing components of the microfluidic probe 500.

Each of the fluid contact ports 522 within the probe interface section 518 can be connected to one or more fluid sources, reservoirs, vacuum sources, and/or waste receptacles as part of an overall fluid handling system. In some aspects, the length of the probe interface section 518 can provide for space for multiple fluid channels within the body of the probe interface section 518, in which fluid or vacuum can be held during a sequential chemistry assay. In some aspects, a subset of the fluid contact ports 522 are connected to one or more fluid sources (e.g., processing fluid, buffer fluid, rinsing fluid, reagent fluid, etc.). In other aspects, a subset of the fluid contact ports 522 can be connected to a vacuum source so as to draw or aspirate fluid up into and/or through the body of the microfluidic probe 500. Accordingly, it can be understood that the fluid contact ports 522 can be arranged to lead into fluidic channels toward one or more injection apertures or one or more aspiration apertures in the processing surface of the probe head 510.

Figure 6:
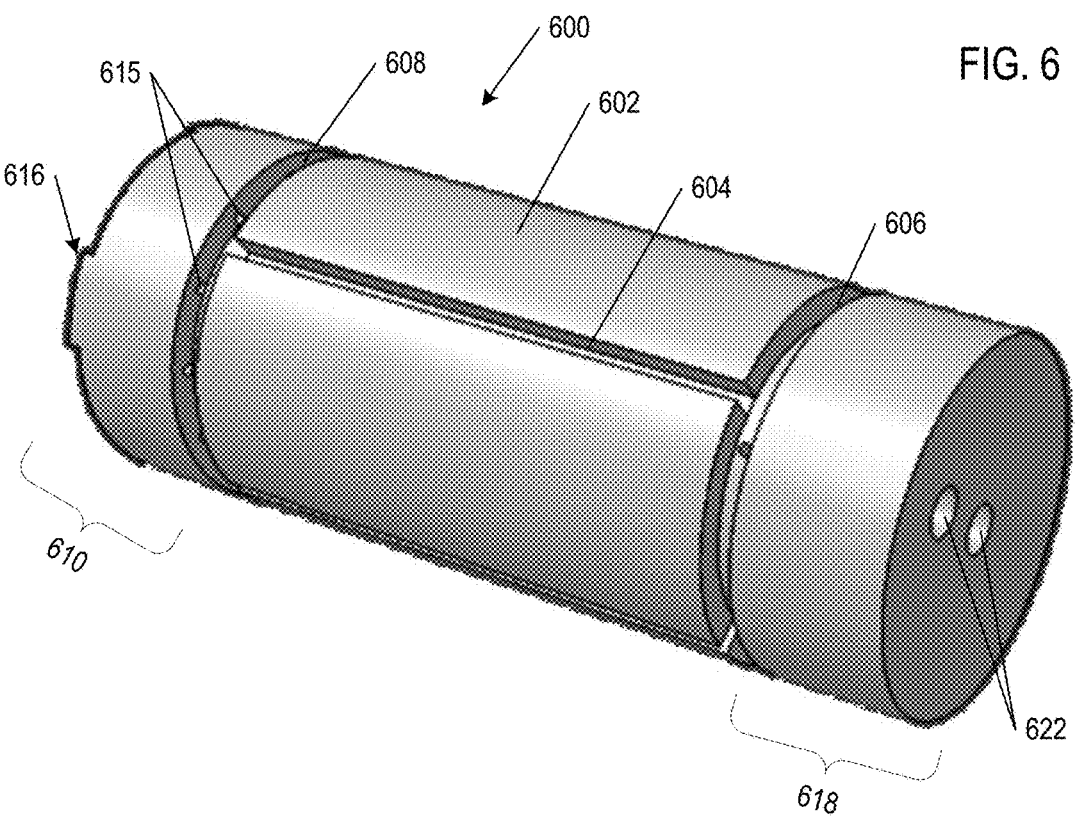
FIG. 6 illustrates the structure for a microfluidic probe with a source fluid connection configuration, according to embodiments of the disclosure.

FIG. 6 illustrates the structure for an exemplary microfluidic probe 600, focusing on the configuration for connection to a source fluid or reservoir. Probe core 602 is shown having exterior channel 604 formed in the exterior surface of probe core 602, running longitudinally along the probe core 602. Microfluidic probe 600 is shown from a perspective view that allows for illustration of fluid contact ports 622 within the probe interface section 618. The probe interface section 618 of microfluidic probe 600 is shown with two (2) fluid contact ports 622 in the uppermost surface of the microfluidic probe 600. Also seen in FIG. 6 are fluidic channels 615 that pass through probe head 610, which are generally used for aspiration, and lead into lower lateral groove 608. As in other variations, lower lateral groove 608, external channels 604, and upper lateral groove 606 are in fluidic communication with each other. Further, aspiration posts 616 along the perimeter or circumference of the probe head 610 are shown projecting outward from the processing surface of probe head 610, giving a relative sense of proportion between the height of the aspiration posts 616 as compared to the probe head 610 for the exemplary microfluidic probe 600. In various aspects aspiration posts 616 can have a height of from thirty micro meters to two hundred micrometers (30 μm-200 μm), or any increment or gradient of length within that range.

Both of the fluid contact ports 622 within probe interface section 618 can be connected to one or more fluid sources, reservoirs, or waste receptacles as part of an overall fluid handling system. In some aspects, one of the fluid contact ports 622 is connected to a fluid source (e.g., processing fluid, buffer fluid, rinsing fluid, reagent fluid, etc.). In other aspects, one of the fluid contact ports 622 is connected to a vacuum source so as to draw or aspirate fluid up into and/or through the body of the microfluidic probe 600. Accordingly, it can be understood that the fluid contact ports 622 can be arranged to lead into fluidic channels toward one or more injection apertures or one or more aspiration apertures in the processing surface of the probe head 10.

In some implementations, the probe interface section 618 as seen in FIG. 6 can be used in combination with a microfluidic probe 400 processing surface 403 as seen in FIG. 4. The arrangement of these ports and associated fluidic channels provides for an MFP head that minimizes mechanical and fluidic interfacing complexity. In other words, one of the two fluid contact ports 622 can be used for injection of a fluid to the MFP head, down to the single, central injection aperture 412, while the other of the two fluid contact ports 622 is used for aspiration, drawing fluid through the aspiration apertures 414 and out to a further section (e.g., waste section) of an overall fluid handling device.

Figure 7A:
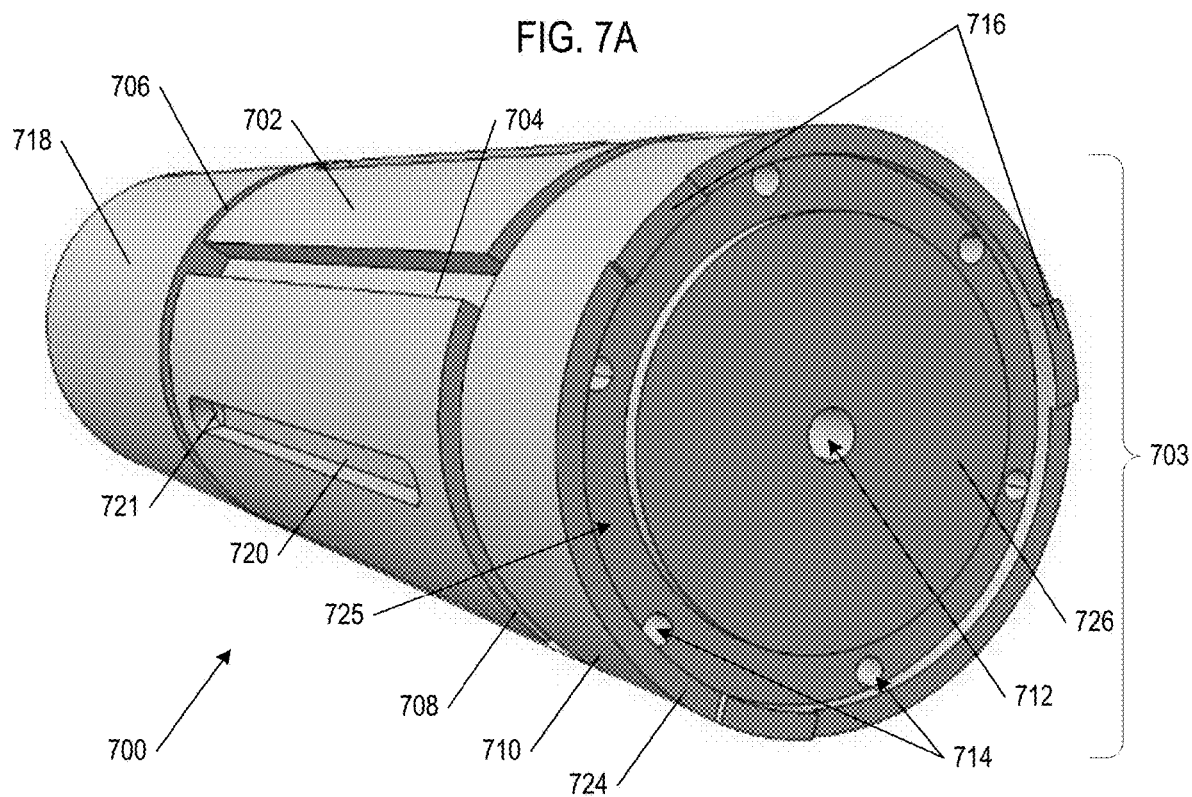
FIG. 7A illustrates the structure for a microfluidic probe and probe head and processing surface for a microfluidic probe head with aspiration posts, according to embodiments of the disclosure.
Figure 7B:
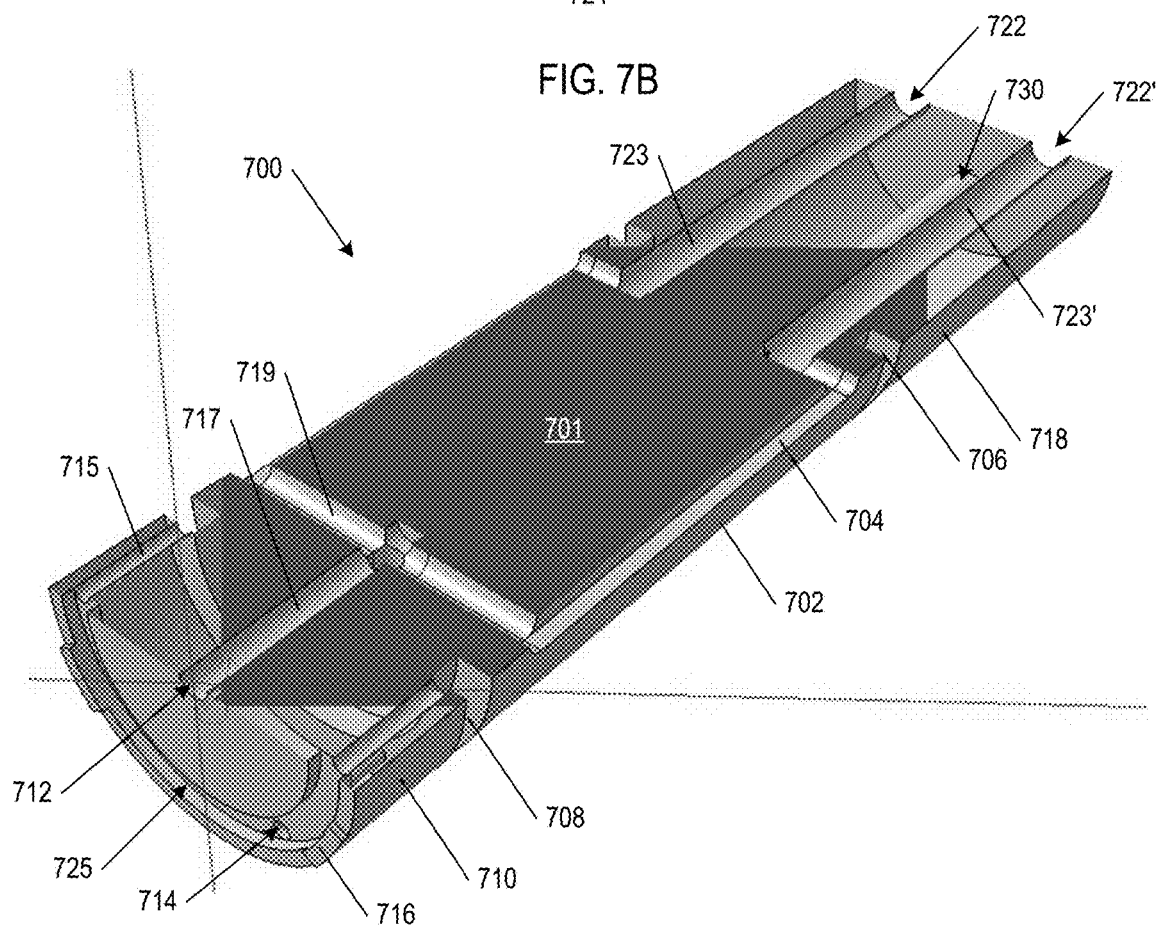
FIG. 7B illustrates a cross-sectional view along the length of the microfluidic probe head shown in FIG. 7A, further showing interior fluidic channels.

FIG. 7A illustrates the structure for an exemplary microfluidic probe 700 and processing surface 703 with aspiration posts 716 for the microfluidic probe 700. FIG. 7B illustrates a cross-sectional view along the length of the microfluidic probe 700 shown in FIG. 7A, further showing interior fluidic channels. As with other exemplary microfluidic probes, microfluidic probe 700 includes a probe core 702 connecting a probe head 710 and a probe interface section 718. The probe core 702 has exterior channels 704, as well as secondary longitudinal channel portions 720 formed in the probe core 702 connecting to probe body ports 721 that lead into the body of probe core 702. A lower groove portion 708 delineates the probe core 702 from the probe head 710, and also provides for a path for fluid flow, typically to aspiration apertures 714 in the processing surface 703, via fluidic channels 715 that pass through probe head 710. An upper groove portion 706 delineates the probe core 702 from the probe interface section 718, and can also provide for a path for fluid flow.

Microfluidic probe 700 further shows aspects of the probe head 710 that can provide for improved HFC. In particular, injection aperture 712 is positioned in the center of a mesa 726, where the mesa 726 can minimize or control the distance between the processing surface 703 and a substrate when the microfluidic probe 700 is in operation. In other words, the height of the mesa 726, or the degree by which the mesa 726 projects downward from the processing surface 703, can control the volume of fluid dispensed through the injection aperture 712, as well as the flow dynamics of that fluid, as that fluid passes over a substrate. Further, on probe head 710, aspiration posts 716 extend outward from a rim 724, where the rim 724 and aspiration posts 716 are flush with the exterior surface and circumference of the probe head 710. In various aspects aspiration posts 716 can have a height of from thirty micrometers to two hundred micrometers (30 μm-200 μm), or any increment or gradient of length within that range.

Aspiration apertures 714 are positioned in a relative recess 725 between mesa 726 and rim 724 (alternatively referred to as a groove or a trench). In some aspects, the structure of the recess 725 between mesa 726 and rim 724 can improve the HFC of the processing surface 703, in part allowing for a concentration of aspiration and corresponding fluidic barrier at that distance from the injection aperture 712. In other words, the recess 725 in which the aspiration apertures 714 are located can assist in creating a homogeneous flow confinement area. Recess 725 can facilitate the HFC, in part, by capturing bubbles that may form in the fluid immersion, thus reducing the probability that such bubbles will enter the aspiration apertures 714. Aspiration apertures 714 are arranged proximate to the perimeter of the processing surface 703, are equidistant from each other around the circumference of the probe head 710, and are equidistant radially from the injection aperture 712 (and by extension, are radially equidistant from the center of the mesa 726). Recess 725 can have a depth (measured upward into the body of microfluidic probe 700, relative to the plane of mesa 726) of from one hundred micrometers to five hundred micrometers (100 μm-500 μm), or any increment or gradient of height within that range.

Looking to the interior body 701 of microfluidic probe 700, the connections and paths of the various fluidic channels can be better understood. Similar to other exemplary embodiments, aspiration apertures 714 lead into aspiration channels 715 that pass through the probe head 710, and lead into lower groove portion 708. As shown, injection aperture 712 leads into injection channel 717, which then flows into radial channels 719 within the body of probe core 702. In this embodiments, injection channel 717 is separate from (not in fluid communication with) the aspiration channels 715. Radial channels 719 lead to exterior channels 704 and then upward into interface channels 723 that open into fluid contact ports 722, 722' at the top of probe interface section 718. Other channels within or along the body of probe core 702, such as secondary longitudinal channel portions 720 can be in fluid communication with aspiration channels 715, lower groove portion 708, and/or upper groove portion 706 to provide a flow route for aspiration of fluids at the processing surface 703.

FIG. 7B illustrates an exemplary interior arrangement of fluidic channels. It can be understood that microfluidic probes as considered herein can have interior channel arrangements with additional fluid channels or alternative configurations and routing of fluid channels. For example, a fluid pathway for one step of injection can be used, formed from fluid contact port 722' and its respective fluid interface channel 723', exterior channel 704, one branch of radial channels 719, and injection channel 717. A subsequent step for injection can be used, formed by a fluid pathway of fluid contact port 722 and its respective fluid interface channel 723, an exterior channel 704 on the opposite side of microfluidic probe 700, another branch of radial channels 719, and injection channel 717. Aspiration can be drawn through aspiration apertures 714, into lower groove portion 708, up along the length of the probe via a channel such as exterior channel 720, into upper groove portion 706 and out of the microfluidic probe through aspiration outlet 730.

In some implementations, the probe interface section 518 as seen in FIG. 5 can be used in combination with a microfluidic probe 700 processing surface 703 as seen in FIGS. 7A and 7B. The arrangement and number of these ports and associated fluidic channels provides for an MFP head that can perform sequential chemistry at the processing surface 703. In such an implementation, one of the four fluid contact ports 522 can be used for injection of one or more fluids to the MFP head, down to the single, central injection aperture 712, while the other one of the four fluid contact ports 722 is used for aspiration, drawing fluid through the aspiration apertures 714 and out to a further section (e.g., waste section) of an overall fluid handling device. This configuration allows for three different injection paths, which can be addressed and used separately for a given protocol. The secondary longitudinal channel portions 720 in the body of probe core 702 can provide for control of the fluid flow paths of from the three separate fluid contact ports 722 used for injection, up until the three respective radial 719 channels merge at injection channel 717.

Figure 8:
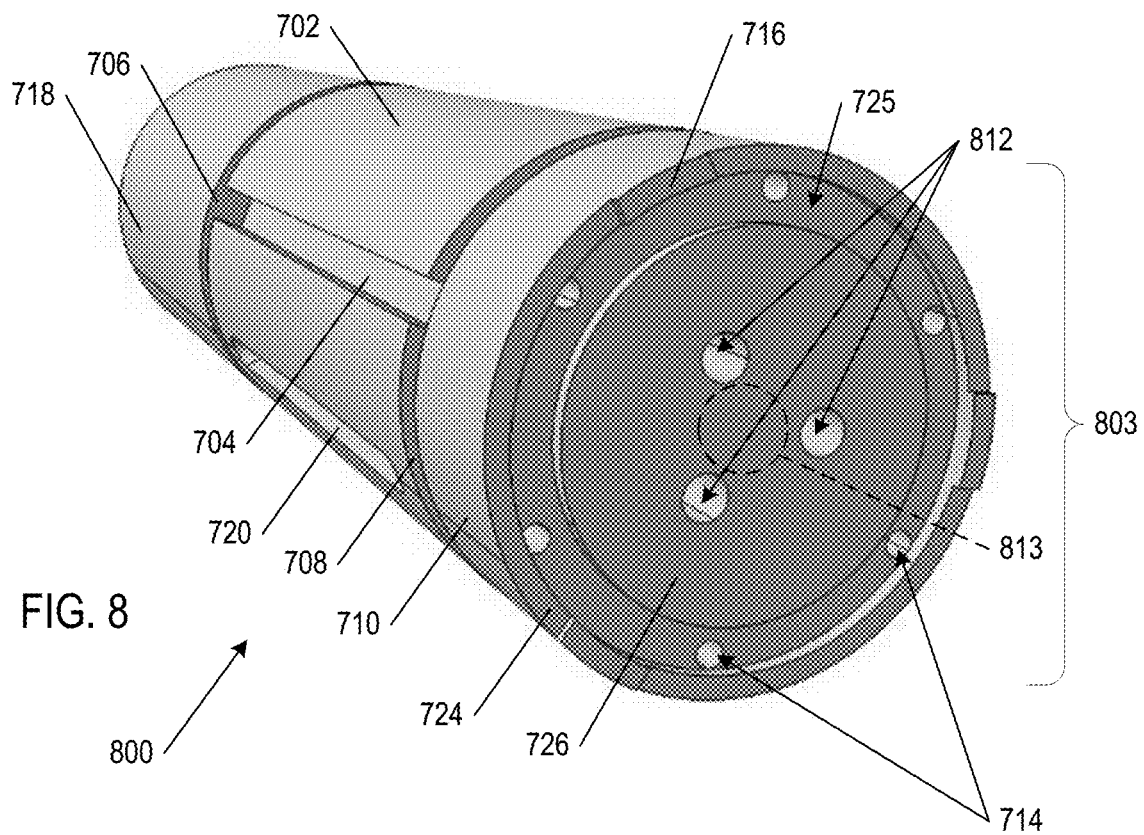
FIG. 8 illustrates the structure for a microfluidic probe and probe head and processing surface for a microfluidic probe head with aspiration posts, according to embodiments of the disclosure.

FIG. 8 illustrates the structure for an exemplary microfluidic probe 800 and processing surface 803 for a microfluidic probe head 710 with aspiration posts 716. Microfluidic probe 800 is similar to the embodiment of the microfluidic probe shown in FIG. 7, except with a different arrangement of injection apertures 812. In particular, processing surface 803 of microfluidic probe 800 has three (3) injection apertures 812 arranged to be at the corners of an equilateral triangle. The injection apertures 812 are centered around the center of the mesa 726, while the aspiration apertures 714 within recess 725 remain arranged proximate to the perimeter of the processing surface 803, equidistant from each other around the circumference of the probe head 710, and are equidistant radially from the center of the mesa 726. The arrangement of injection apertures 812 provides for a space in between the triangular corners of their arrangement, which can be referred to as a stagnation space 813. Within the stagnation space 813, the flow of fluid deposited from the injection apertures 812 can eddy and be recirculated during operation of the microfluidic probe 800. Accordingly, substances or cells within the injected fluid can reside for a relatively longer period of time within the stagnation space 813, and thus have more time to bind or deposit material in the injection fluid (e.g., cells) onto an underlying substrate or sample surface. Further, the fluid flow from each individual injection aperture 812 to the surrounding aspiration apertures 714 will be biased such that injected fluid from any one of the three injection apertures 812 will tend to be drawn toward the relatively closest aspiration apertures 714.

It can be appreciated that alternative embodiments of the microfluidic probe 800 as in FIG. 8 could be formed with a different number of injection apertures in other arrangements. For example, a processing surface with four injection apertures can be arranged in a square layout, a processing surface with five injection apertures can be arranged in a pentagon layout, a processing surface with six injection apertures can be arranged in a hexagon layout, and the like. Further, the distance between injection apertures in all such arrangements can be varied, to increase or decrease the size of the stagnation space, and to also vary the control of a fluid lamella between the injection apertures and the aspiration apertures.

Figure 9:
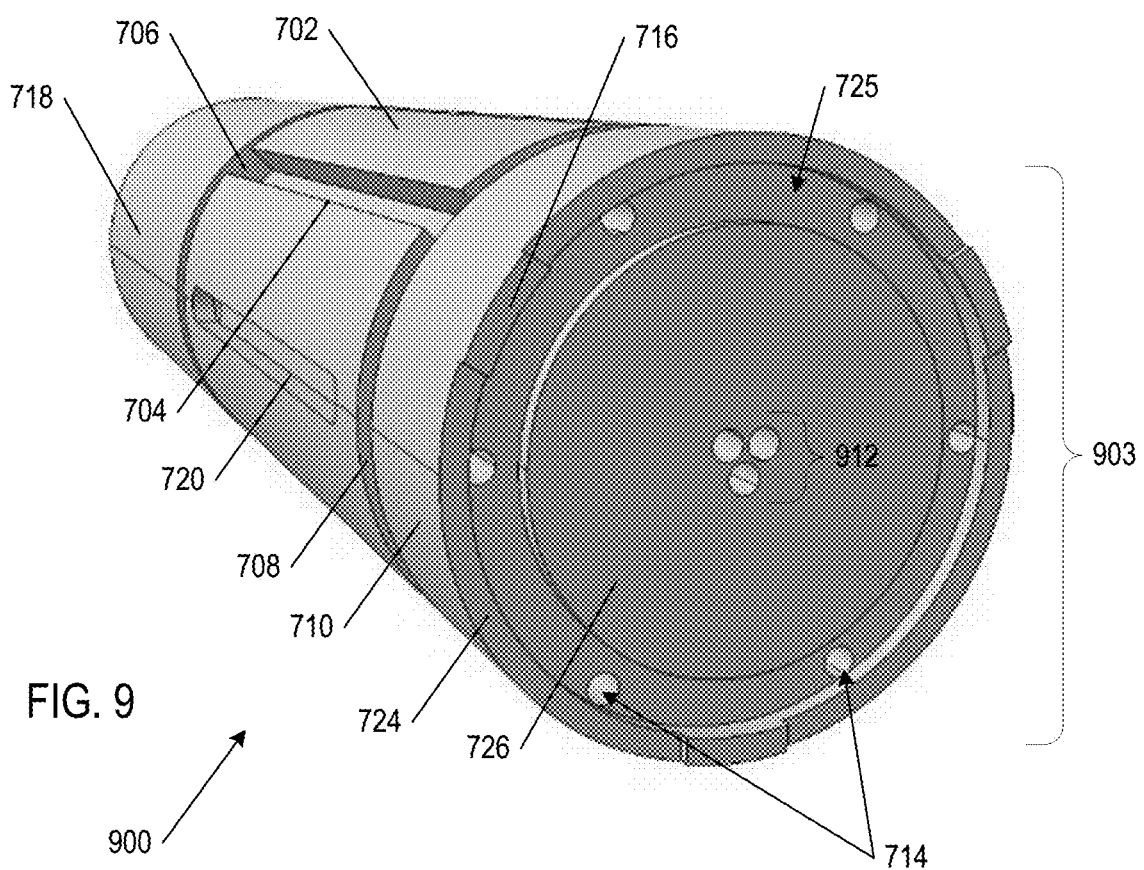
FIG. 9 illustrates the structure for a microfluidic probe and probe head and processing surface for a microfluidic probe head with aspiration posts, according to embodiments of the disclosure.

FIG. 9 illustrates the structure for an exemplary microfluidic probe 900 and processing surface 903 for a microfluidic probe head 710 with aspiration posts 716. Microfluidic probe 900 is similar to the embodiments of the microfluidic probe shown in FIG. 7 and FIG. 8, except with a different arrangement of injection apertures 912. In particular, processing surface 903 of microfluidic probe 900 has three (3) injection apertures 912 arranged to be at the corners of an equilateral triangle. In contrast with the embodiment of FIG. 8, the three injection apertures 912 are positioned relatively close to each other, such that the injection apertures can function similarly to a single injection aperture. The injection apertures 912 remain centered around the center of the mesa 726, while the aspiration apertures 714 within recess 725 remain arranged proximate to the perimeter of the processing surface 903, equidistant from each other around the circumference of the probe head 710, and are equidistant radially from the center of the mesa 726. An advantage of using the three injection apertures 912 at the center of the processing surface 903 incudes, but is not limited to, separate or graduated control of injection pressure through each individual injection aperture 912. Further, the fluid flow from each individual injection aperture 912 to the surrounding aspiration apertures 714 will be biased such that injected fluid from any one of the three injection apertures 912 will tend to be drawn toward the relatively closest aspiration apertures 714.

It can be appreciated that alternative embodiments of the microfluidic probe 900 as in FIG. 9 could be formed with a different number of injection apertures in other arrangements. For example, a processing surface with four injection apertures can be arranged in a square layout, a processing surface with five injection apertures can be arranged in a pentagon layout, a processing surface with six injection apertures can be arranged in a hexagon layout, and the like. It can be further appreciated that processing surface 903 of microfluidic probe 900 is similar to processing surface 803 of microfluidic probe 800 consider, but with the distance between injection apertures reduced such that there is effectively no stagnation space generated beneath the processing surface 903 of microfluidic probe 900.

Both of the three-injection aperture embodiments of the microfluidic probe as shown in FIG. 8 and FIG. 9 can have corresponding fluidic channels passing through the probe core that do not merge within MFP head. Rather, each injection channel outlets from the MFP head separately, which can provide for a further reduction in cross-contamination, and allow for more precise addressing and configuration of flow paths for chemistry testing. Accordingly, each of the injection apertures can be ultimately in fluid communication with a different fluid source or reservoir, allowing for complex chemistry assays to be conducted through the MFP head without the different fluids mixing or picking up residual amounts of other fluids. In alternative embodiments, two of the respective injection aperture fluidic channels, or all three, can merge within the MFP head, to allow for further control and flexibility in chemistry testing and injection flow.

In alternative aspects, the microfluidic probes having three central apertures as shown in FIG. 8 and FIG. 9 can be used to concurrently or sequentially inject different fluids through each aperture. This implementation can also be applied to any other processing surface having more than one injection aperture. In other alternative aspects, the multiple centrally located apertures can be used such a subset of the apertures are used for injection while the remaining subset of apertures are used for aspiration. More specifically, The microchannel and aperture arrangements within the MFP head as shown in FIGS. 8 and 9 provide a structure that can be efficiently used for sequential chemistry processes. Each of the three apertures 812, 912 can be connected to different fluid sources, thereby allowing for the alternating or sequential injection of sample fluid, reagents, buffer, washing fluid, and the like. The sequence of injected fluids through the separate apertures 812, 912 can be set according to any given experimental design. An advantage in the use of the separate apertures 812, 912 is that, with apertures (and corresponding fluid supply channels) dedicated to depositing a single fluid at a time, the amount of residual solution or sample carried from one injection process into a subsequent injection process is significantly reduced, and potentially eliminated. It should be understood that further variations of MFP heads can use any number of injection apertures for sequential chemistry, within the structural limitations of the size of the related mesa and the number of fluid supply channels that can be fit in the overall probe body. In some implementations, individual fluid supply channels or injection apertures can be used by more than one injection aperture, with only minimal concern for carry-over of solution or particles from one step of a sequential process to the next. For example, the same channel or injection aperture could be used sequentially for a rinse and then for an anti-globulin injection.

Figure 10A:
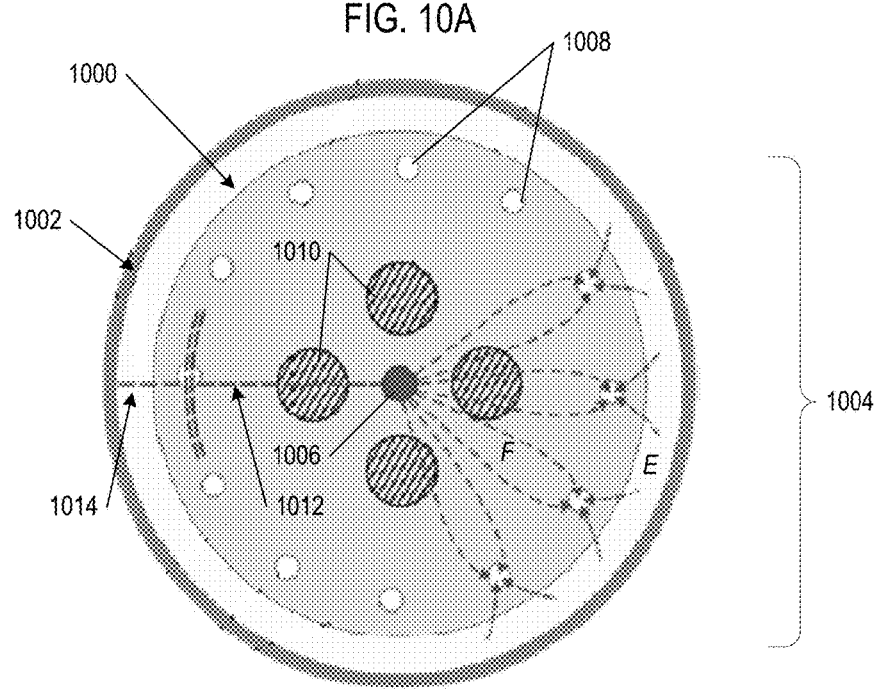
FIG. 10A illustrates a plan view of a microfluidic probe head processing surface, further showing indications of fluid flow, according to embodiments of the disclosure.
Figure 10B:
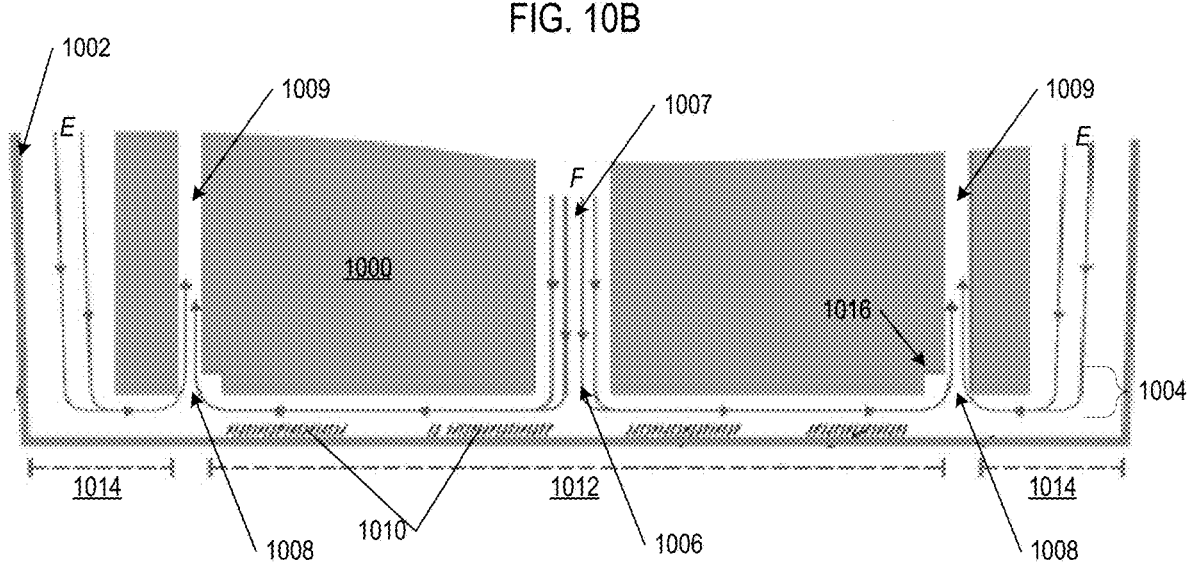
FIG. 10B illustrates a cross-sectional view of the microfluidic probe head shown in FIG. 10A, further showing indications of fluid flow.

FIG. 10A illustrates a plan view of an exemplary microfluidic probe head 1000 and its processing surface 1004, further showing indications of fluid flow. FIG. 10B illustrates a cross-sectional view of the microfluidic probe head 1000 shown in FIG. 10A, also showing further indications of fluid flow. The microfluidic probe head 1000 is shown positioned at an operational position within a sample well 1002 (e.g., a microtiter plate well), where the processing surface 1004 has a single injection aperture 1006 located in the center of the processing surface 1004, and twelve (12) aspiration apertures 1008, having rotational symmetry with regard to each other, arrayed along the perimeter of the processing surface 1004. It is understood that the number of aspiration apertures 1008 can vary between embodiments of microfluidic probes heads as considered herein. Processing fluid F injected through injection aperture 1006 (via injection microchannel 1007) is drawn toward the aspiration apertures 1008, through which a vacuum pulls fluid up and out of the sample well 1002 (via aspiration microchannels 1009). At the bottom of the sample well 1002, target regions 1010 are located within the processing region 1012 of the processing surface 1004. The processing region 1012 can be considered to be the space underneath the processing surface 1004 and above the sample well 1002 floor where the flow paths of fluid delivered through the injection aperture 1006 are controlled. Due to the configuration of the processing surface 1004, processing fluid F injected through the injection aperture 1006 has an optimized or maximized residence time over the target regions 1010, which can have specific substrates or other surfaces loaded with target receiving material (e.g., samples, reagents, etc.). Accordingly, surfaces in these target regions 1010 be saturated or receive as high a density of the delivered processing fluid F and any material in suspension (e.g., further samples, further reagents, cells) in the delivered processing fluid F.

The volume of environmental fluid E (e.g., buffer, rinsing fluid, reagent fluid, etc.) surrounding the microfluidic probe head 1000 is also drawn up into aspiration apertures 1008, around the outside surface of the microfluidic probe head 1000, which can be at least partially immersed in the environmental fluid E. The combination of the draw from the aspiration apertures 1008 and the environmental fluid E provides for a "clean" region 1014 where the processing fluid F is prevented from flowing. In other words, the draw of the aspiration apertures 1008, in combination with the presence and radially inward flow of the environmental fluid E, provides for the hydrodynamic flow confinement of the processing fluid F, maintaining the clean region 1014 as without sample, cells, reagent, or other components within or carried by the processing fluid F.

At each aspiration aperture 1008, processing surface 1004 can include a small step or indentation on the side of the aspiration aperture 1008 closest to the injection aperture 1006. This mesa step 1016 can aid in directing processing fluid F flow coming from the injection aperture 1006 up into the injection apertures 1008 and can further aid in developing a fluidic barrier at the interface of the processing fluid F and the environmental fluid E. In some aspects, the configuration of the mesa step 1016 effectively positions the aspiration apertures 1006 within a ring-shaped groove along the perimeter of the processing surface 1004. This ring-shaped groove homogenizes the flow of environmental fluid E and allows for the formation of a smoother circular flow confinement. The processing surface 1004 can further include aspiration posts (not shown) arranged at or along positions on the perimeter of the processing surface 1004.

Figure 11A:
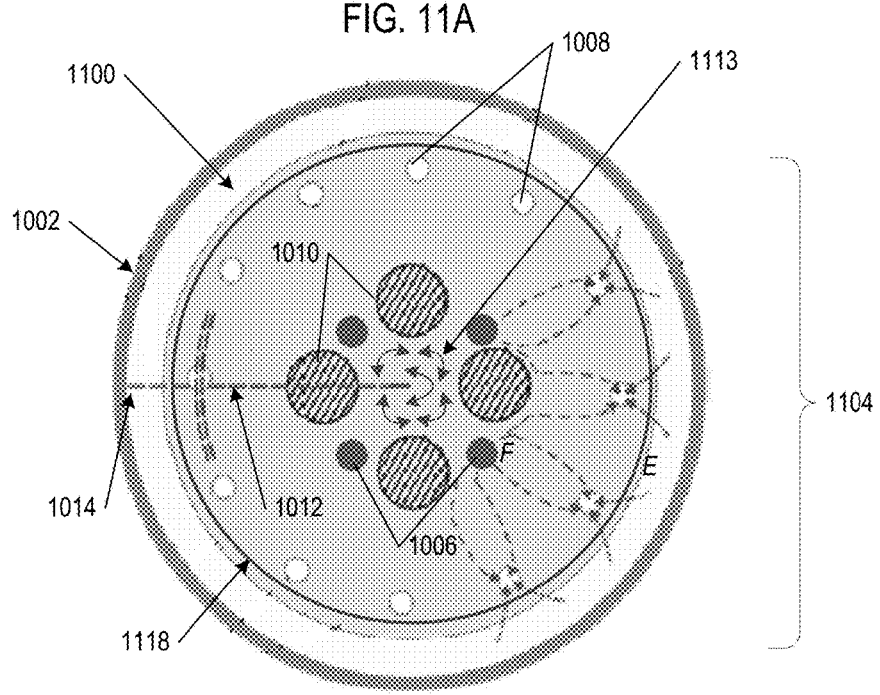
FIG. 11A illustrates a plan view of a microfluidic probe head processing surface, further showing indications of fluid flow, according to embodiments of the disclosure.
Figure 11B:
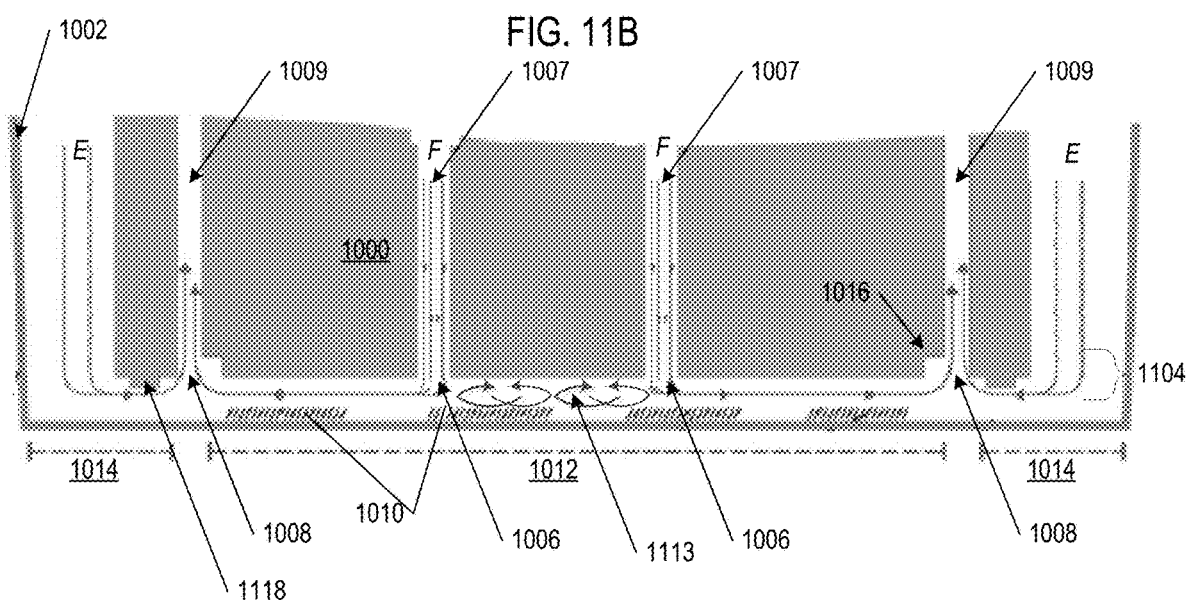
FIG. 11B illustrates a cross-sectional view of the microfluidic probe head shown in FIG. 11A, further showing indications of fluid flow.

FIG. 11A illustrates a plan view of an exemplary microfluidic probe head 1100 and its processing surface 1104, further showing indications of fluid flow. FIG. 11B illustrates a cross-sectional view of the microfluidic probe head 1100 shown in FIG. 11A, also showing further indications of fluid flow. The microfluidic probe head 1100 is shown positioned at an operational position within a sample well 1002 (e.g., a microtiter plate well), where the processing surface 1104 has a four (4) injection apertures 1006 located in the center of the processing surface 1104, having rotational symmetry with regard to each other, arrayed around the center of the processing surface 1104, general forming a square layout with the injection apertures 1006 positioned at the corners of the square. The processing surface 1104 also has twelve (12) aspiration apertures 1008, having rotational symmetry with regard to each other, arrayed along the perimeter of the processing surface 1104. It is understood that the number of aspiration apertures 1008 can vary between embodiments of microfluidic probes heads as considered herein. Processing fluid F injected through injection apertures 1006 (via injection microchannels 1007) is drawn toward the aspiration apertures 1008, through which a vacuum pulls fluid up and out of the sample well 1002 (via aspiration microchannels 1009). At the bottom of the sample well 1002, target regions 1010 are located within the processing region 1012 of the processing surface 1104. The processing region 1012 can be considered to be the space underneath the processing surface 1004 and above the sample well 1002 floor where the flow paths of fluid delivered through the injection aperture 1006 are controlled. Due to the configuration of the processing surface 1104, processing fluid F injected through the injection aperture 1006 has an optimized or maximized residence time over the target regions 1010, which can have specific substrates or other surfaces loaded with target receiving material (e.g., samples, reagents, etc.). Accordingly, surfaces in these target regions 1010 be saturated or receive as high a density of the delivered processing fluid F and any material in suspension (e.g., further samples, further reagents, cells) in the delivered processing fluid F.

The volume of environmental fluid E (e.g., buffer, rinsing fluid, reagent fluid, etc.) surrounding the microfluidic probe head 1000 is also drawn up into aspiration apertures 1008, around the outside surface of the microfluidic probe head 1000, which can be at least partially immersed in the environmental fluid E. The combination of the draw from the aspiration apertures 1008 and the environmental fluid E provides for a "clean" region 1014 where the processing fluid F is prevented from flowing. In other words, the draw of the aspiration apertures 1008, in combination with the presence and radially inward flow of the environmental fluid E, provides for the hydrodynamic flow confinement of the processing fluid F, maintaining the clean region 1014 as without sample, cells, reagent, or other components within or carried by the processing fluid F.

The arrangement of the four aspiration apertures 1006 on the processing surface 1104 provides for a stagnation space 1113 in between the aspiration apertures 1006, and vertically between the processing surface 1104 and the bottom of the sample well 1002. Within the stagnation space 1113, the flow of fluid deposited from the injection apertures 1006 can eddy and be recirculated during operation of the microfluidic probe 1100. Accordingly, substances or cells within the injected fluid F can reside for a relatively longer period of time within the stagnation space 1113, and thus have more time to bind or deposit material in the injection fluid (e.g., cells) onto an substrates in the target regions 1010 or elsewhere on the bottom surface of the sample well 1002. Further, the fluid flow from each individual injection aperture 1006 to the surrounding aspiration apertures 1008 will be biased such that injected fluid from any one of the four injection apertures 1006 will tend to be drawn toward the relatively closest aspiration apertures 1008.

Similarly to the embodiments seen in FIGS. 8 and 9, each of the four injection apertures can connect to separate fluidic channels. Thus, each injection aperture (or a subset thereof) can be ultimately in fluid communication with a different fluid source or reservoir, allowing for complex sequential chemistry assays to be conducted through the MFP head without the different fluids mixing or picking up residual amounts of other fluids.

While the aspiration apertures 1006 of processing surface 1104 are arranged in a square layout, it can be appreciated that any number of aspiration apertures 1006 can be arrayed within a processing surface for MFP heads as considered herein, with different shaped layouts. For example, a processing surface with three injection apertures can be arranged in a triangular layout, a processing surface with five injection apertures can be arranged in a pentagon layout, a processing surface with six injection apertures can be arranged in a hexagon layout, and the like.

At each aspiration aperture 1008, processing surface 1004 can include a small step or indentation on the side of the aspiration aperture 1008 closest to the injection aperture 1006. This mesa step 1016 can aid in directing processing fluid F flow coming from the injection aperture 1006 up into the injection apertures 1008 and can further aid in developing a fluidic barrier at the interface of the processing fluid F and the environmental fluid E. In some aspects, the configuration of the mesa step 1016 effectively positions the aspiration apertures 1006 within a ring-shaped groove along the perimeter of the processing surface 1104. This ring-shaped groove homogenizes the flow of environmental fluid E and allows for the formation of a smoother circular flow confinement.

The processing surface 1104 of microfluidic probe head 1100 can further include a circular protrusion 1118 extending along the perimeter or circumference of the processing surface 1104, positioned around or outside of the aspiration apertures 1006. The circular protrusion 1118 provides for a physical or mechanical barrier that can increase the flow velocity or shear below the circular protrusion 1118, and thereby help in shielding the processing region 1012 from exposure to unwanted fluids or material. Similarly, the processing surface 1104 can further include aspiration posts (not shown) arranged at or along positions on the perimeter of the processing surface 1104.

In both of the exemplary microfluidic probe heads seen in FIGS. 10A, 10B, 11A, and 11B, it can be understood that with the processing surface positioned in proximity with a sample surface (which can be immersed under an environmental fluid E), the flow of processing fluid F, which can be a non-Euclidian fluid and/or include cells, is routed by injection channels 1007 through injection apertures 1006 downward toward the bottom of the sample well 1002. Accordingly, any cells in the processing fluid F are pushed directed downward into contact with the bottom of the sample well 1002 and particularly with any substrate or other receiving surface in the target regions 1010. In some aspects, the target regions can include reagents or structures where specific bindings, chemistries, and reactions can take place. Further, the processing fluid F is drawn outward in a radial direction from the injection aperture 1006 toward the aspiration apertures 1008, where the draw of the aspiration flattens out the processing fluid F lamella over the bottom of the sample well 1002 and the target regions 1010. Both the environmental fluid E and the processing fluid F can be aspirated from the processing surface and sample well 1002 area through the single liquid aspiration apertures 1006. The mixed liquid volume (which can also include other fluids such as buffers) are routed through aspiration microchannels 1009 away from the MFP head, and ultimately to a waste receptacle.

Figure 12A:
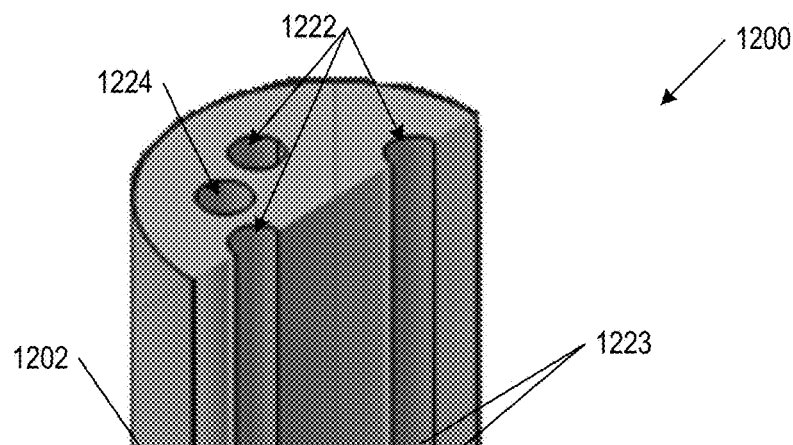
FIG. 12A illustrates a cross-sectional view of a microfluidic probe head according to embodiments of the disclosure.
Figure 12B:
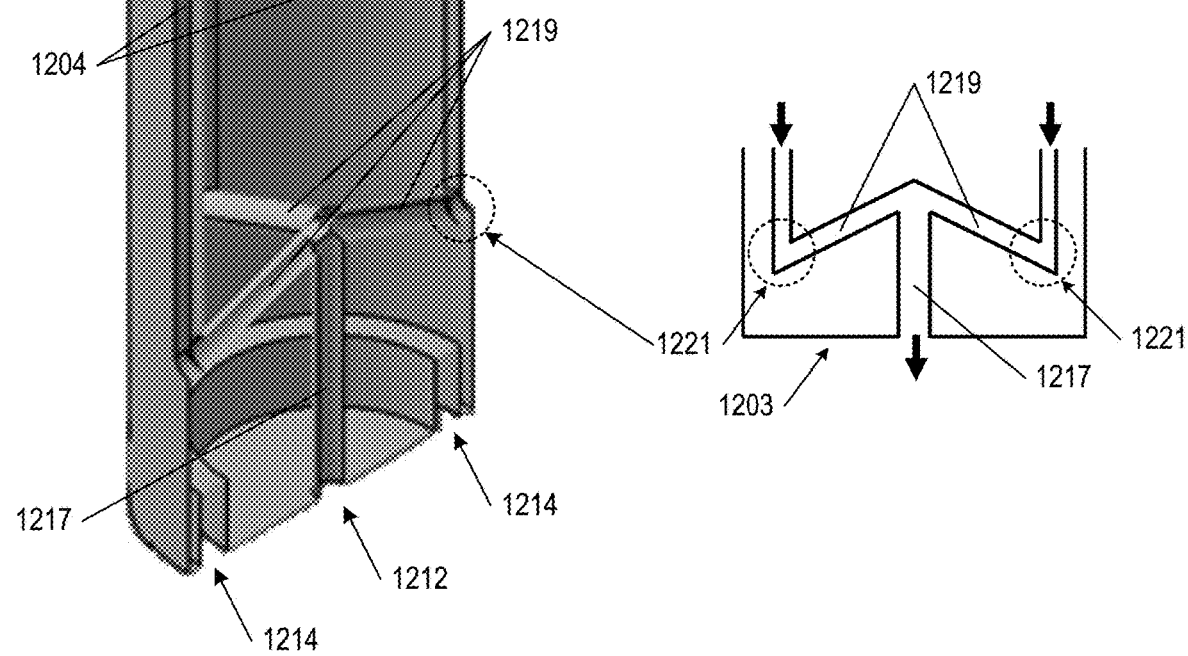
FIG. 12B shows indications of fluid flow for a section of the microfluidic probe head shown in FIG. 12A.

FIG. 12A illustrates a cross-sectional view of a microfluidic probe head 1200, with FIG. 12B providing a further schematic of flow through a portion of the internal channels shown in FIG. 12A. Looking to the interior body 1201 of probe core 1202, the connections and paths of the various fluidic channels can be better understood. Similar to other exemplary embodiments, fluid contact ports 1222 at the top of the microfluidic probe 1200 can be used for the introduction of fluid into interface channels 1223, that in turn lead to exterior channels 1204 running along the outside surface of the probe core 1202. In contrast with other embodiments, radial channels 1219 extending inward into probe core 1202 also extend upward within the interior body 1201. The intersection between an exterior channel 1204 and radial channel 1219 can be referred to as a channel elbow 1221. At each channel elbow 1221, each respective radial channel 1219 rises at an incline of from about 5° to about 30° (relative to the plane defined by the processing surface 1203) until the radial channel 1219 meets at the top of injection channel 1217. In other aspects, the angle of incline for a radial channel 1219 at a channel elbow 1221 can be less than 5° (e.g., 1°) or greater than 30° (e.g., 45°, 60°, etc.). Accordingly, through each separate fluid contact port 1222 and radial channel 1219, different fluids can be sequentially injected through the injection port 1212 at the processing surface 1203 of the microfluidic probe head 1200. Aspiration apertures 1214 positioned around injection port 1212 can remove liquid from under the processing surface 1203, back up through the probe core via pumping or vacuum drawn through an aspiration fluid port 1224 dedicated to egress of fluids.

The presence of channel elbows 1221 in the internal injection path functions to hinder sedimentation of analytes (e.g., red blood cells) within a microtiter well. Rather, amounts of analytes that would otherwise leak residually from the injection port 1212 instead reside in the bend or crook of the channel elbow 1221. The prevention of leaking sedimentation can thus reduce or eliminate the need for additional washing steps when performing sequential chemical reactions progressively through the distinct fluid paths. After completing a set of sequential chemical injections and reactions, the internal fluid paths can be rinsed to wash any residual analytes from the crook of the channel elbows 1221.

In further alternative embodiments, as can be inferred from the processing surface layouts and mesas of the microfluidic probe heads considered above, liquid can be injected or aspirated by additional apertures surrounding the first aspiration apertures to improve confinement or for rinsing purposes. Indeed, in some applications, it important to remove non-specifically bound cells and also cells that remain on the surface due to sedimentation.

In some implementations, rinsing can take place either during the deposition process (continuous rinsing) or after the process (sequential rinsing). In support of that functionality, additional aspiration apertures, or a subset of aspiration apertures can allow for a rinsing zone or cycle to be created. Rinsing fluids can be injected via the injection apertures (being switched between fluid sources elsewhere in the overall fluid handling system), or though multi-purposed aspiration apertures.

In other implementations, the operation of a microfluidic probe head can include an oscillation sequence, which can create a liquid disturbance within the HFC to counteract non-binding analyte sedimentation and improve analyte aspiration. Such oscillation can be coordinated with an different aspiration rate than used concurrently with fluid injection. In some aspects, the MFP head can run through three cycles of twelve oscillations over a specific period of time (e.g., 30 seconds) that move the MFP head about 300 μm, where the oscillation protocol can be executed periodically (e.g., after every 30 seconds of fluid injection). This approach can also reduce or eliminate the need for a separate washing step to remove miscellaneous analyte sedimentation. In some aspects, aspiration from the lateral aspirators (arranged toward the perimeter of a processing surface) during an oscillation sequence can have a draw of about one hundred microliters per minute (100 μL/min). In further aspects, the injection aperture can be repurposed to have its flow direction reversed to also have a draw, which can be about one hundred microliters per minute (100 μL/min), during an oscillation sequence. It should be understood that greater or lesser (within an order of magnitude) numbers of cycles, numbers of oscillation movements, oscillation distances, and aspiration rates can be used for such oscillation processes.

From FIGS. 2A-12B it can be understood that injection apertures, aspiration apertures, internal channels, mechanical barriers, and other mesa structures can have various sizes and shapes, which can be selected for particular applications as appropriate. The exemplary distances and sizes articulated above should not be considered to be limiting. Further, each of the injection apertures can be configured to deposit fluids at a particular rate of flow, ranging from one-half microliter per minute (0.5 μL/min) to eighty microliters per minute (80 μL/min), and at specific increments, gradients, and ranges therein. In specific embodiments, injection apertures can deposit fluids with a rate of flow of about two microliters per minute (2 μL/min), a rate of flow of about three microliters per minute (3 μL/min), or a rate of flow of about five microliters per minute (5 μL/min). Similarly, each of the aspiration can be configured to vacuum fluids at a particular rate of draw, ranging from one microliter per minute (1 μL/min) to eighty microliters per minute (80 μL/min), and at specific increments, gradients, and ranges therein. In specific embodiments, injection apertures can deposit fluids with a rate of flow of about ten microliters per minute (10 μL/min), a rate of flow of about fifteen microliters per minute (15 μL/min), or a rate of flow of about twenty microliters per minute (20 μL/min).

In other embodiments, of the microfluidic probes considered herein, the dynamics of the processing surface and HFC can be controlled by a variety of means, including, but not limited to, increasing or decreasing the electrical resistivity of the probe head, changing the textures of the materials forming the probe, or changing the pressures of fluid flow.

In some embodiments, the MFP heads as considered herein fan further be constructed to be disposable devices. By using disposable MFP heads, removing and replacing the MFP heads between assays or tests, cleaning requirements would be further reduced and cross-contamination concerns could be almost completely eliminated.

While the present disclosure has been described with reference to a limited number of embodiments, variants and the accompanying drawings, it will be understood by those skilled in the art that various changes may be made and equivalents may be substituted without departing from the scope of the present disclosure. In particular, a feature (device-like or method-like) recited in a given embodiment, variant or shown in a drawing may be combined with or replace another feature in another embodiment, variant or drawing, without departing from the scope of the present disclosure. Various combinations of the features described in respect of any of the above embodiments or variants may accordingly be contemplated, that remain within the scope of the appended claims. In addition, many minor modifications may be made to adapt a particular situation or material to the teachings of the present disclosure without departing from its scope. Therefore, it is intended that the present disclosure not be limited to the particular embodiments disclosed, but that the present disclosure will include all embodiments falling within the scope of the appended claims. In addition, many other variants than explicitly touched above can be contemplated. For example, other materials than silicon or glass can be contemplated for layers, such as, e.g., PDMS or other elastomers, hard plastics (e.g., PMMA, COC, PEEK, PTFE, etc.), ceramics, or stainless steel.

It can be further appreciated that the microfluidic probe heads considered and disclosed herein can have application in areas beyond chemistry and microbiology. For example, ink jet printer heads can be formed having injection-aspirator mesa arrangements as shown herein. Alternatively, three-dimensional (3D) printing apparatuses can have such injection-aspirator mesa arrangements that can, for example, control resin deposition within a desired flow containment area.

It is appreciated that instrumentation and systems employing the MFP heads disclosed herein can include a microprocessor, and can further be a component of a processing device that controls operation of the testing procedures and sample analysis. The processing device can be communicatively coupled to a non-volatile memory device which may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

The above description is illustrative and is not restrictive, and as it will become apparent to those skilled in the art upon review of the disclosure, that the present disclosure may be embodied in other specific forms without departing from the essential characteristics thereof. For example, any of the aspects described above may be combined into one or several different configurations, each having a subset of aspects. Further, throughout the foregoing description, for the purposes of explanation, numerous specific details were set forth in order to provide a thorough understanding of the disclosure. It will be apparent, however, to persons skilled in the art that these embodiments may be practiced without some of these specific details. These other embodiments are intended to be included within the spirit and scope of the present disclosure. Accordingly, the scope of the disclosure should, therefore, be determined not with reference to the above description, but instead should be determined with reference to the following and pending claims along with their full scope of legal equivalents.

What is claimed is:

1. A microfluidic probe head configured to operate with a sample well, comprising:
   a processing surface at one end of the microfluidic probe head, configured to interact with fluids within a processing region proximate to the processing surface, the processing surface comprising a center and an outer edge defining a perimeter of the processing surface;
   one or more injection apertures disposed within an inner region located at or around the center of the processing surface;
   a plurality of aspiration apertures disposed within an outer region spaced from the inner region and extending to the outer edge of the processing surface, the plurality of aspiration apertures being radially distributed around the one or more injection apertures, wherein a distance of the plurality of aspiration apertures from the outer edge of the processing surface is from 10% to 80% of a diameter of the sample well; and
   two or more posts extending outward from the processing surface, the two or more posts being configured to form a fluidic barrier comprising a turbulent flow at the plurality of aspiration apertures and establishing a height of the processing region, wherein at least a portion of a wall of a post of the two or more posts is located about an equal radial distance along with at least one of the plurality of aspiration apertures from the center of the processing surface such that the fluid interacts with the posts during aspiration to form the fluidic barrier comprising the turbulent flow.

2. The microfluidic probe head of claim 1, wherein the processing surface has three injection apertures arranged in a triangular configuration.

3. The microfluidic probe head of claim 2, wherein the three injection apertures are spaced apart from each other such that the processing region includes a stagnation space formed between the three injection apertures.

4. The microfluidic probe head of claim 2, wherein the three injection apertures are each connected to different fluid sources.

5. The microfluidic probe head of claim 1, wherein the processing surface has four injection apertures arranged in a square configuration.

6. The microfluidic probe head of claim 5, wherein the four injection apertures are spaced apart from each other such that, the processing region includes a stagnation space formed between the four injection apertures.

7. The microfluidic probe head of claim 5, wherein two or more of the four injection apertures are connected to different fluid sources.

8. The microfluidic probe head of claim 1, wherein the plurality of aspiration apertures comprise one or more circular holes arrayed along the perimeter of the processing surface and are located within the outer region.

9. The microfluidic probe head of claim 1, wherein the plurality of aspiration apertures are located within a recess formed within the processing surface.

10. The microfluidic probe head of claim 1, wherein the two or more posts extend 0.1 mm outward from the processing surface.

11. The microfluidic probe head of claim 1, comprising four posts, arranged equidistantly from each other around the perimeter of the processing surface and located within the outer region.

12. The microfluidic probe head of claim 11, wherein the plurality of aspiration apertures are positioned in between the four posts, arranged around the perimeter of the processing surface and located within the outer region.

13. The microfluidic probe head of claim 11, wherein each of the four posts is paired with an aspiration aperture positioned adjacent to each post on a side of the post facing the one or more injection apertures.

14. The microfluidic probe head of claim 1, further comprising a probe interface section at an end of the microfluidic probe head distal from the processing surface, the probe interface section comprising fluid contact ports configured to connect the microfluidic probe head with one or more fluid sources and a vacuum source.

15. The microfluidic probe head of claim 14, wherein the probe interface section includes four fluid contact ports, wherein three of the fluid contact ports are connected to one or more fluid source reservoirs, and wherein a fourth fluid contact port is connected to the vacuum source.

16. The microfluidic probe head of claim 1, wherein the at least a portion of the wall of a post of the two or more posts is flush with fluidic channel surface associated with at least one of the plurality of aspiration apertures.

17. A method of operating the microfluidic probe head according to claim 1, the method comprising:
    positioning the microfluidic probe head in proximity with a substrate holding material to be processed, such that the processing surface faces the substrate; and
    injecting a processing liquid via the one or more injection apertures while aspirating liquid from the plurality of aspiration apertures, to process the substrate.

18. The method according to claim 17, wherein the processing liquid is a heterogeneous suspension comprising cells, and wherein injecting processing liquid is performed so as to deposit cells of this heterogeneous suspension onto a sample surface.

19. The method according to claim 17, wherein the steps of injecting the processing liquid and aspirating liquid are performed so as to maintain a hydrodynamic flow confinement of the injected processing liquid between the one or more injection apertures and the plurality of aspiration apertures.

20. The microfluidic probe head of claim 1, wherein a distance of aspiration apertures from the outer edge of the processing surface of the microfluidic probe (MFP) head is configured to be from about 10% to about 20% of a diameter of a sample well in which the MFP head is designed to operate.

21. The microfluidic probe head of claim 1, wherein a size of the one or more injection apertures is a function of the height of each of the two or more posts.

\* \* \* \* \*